(12) United States Patent
Ishiura et al.

(10) Patent No.: US 10,675,186 B2
(45) Date of Patent: Jun. 9, 2020

(54) FABRIC AND LIQUID ABSORBING ARTICLE

(71) Applicant: Murata Manufacturing Co., Ltd., Nagaokakyo-shi, Kyoto-fu (JP)

(72) Inventors: Yutaka Ishiura, Nagaokakyo (JP); Nobuhito Tsubaki, Nagaokakyo (JP); Satoshi Takeshima, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 143 days.

(21) Appl. No.: 16/128,689

(22) Filed: Sep. 12, 2018

(65) Prior Publication Data

US 2019/0008687 A1 Jan. 10, 2019

Related U.S. Application Data

(63) Continuation of application No. PCT/JP2018/016534, filed on Apr. 24, 2018.

(30) Foreign Application Priority Data

May 31, 2017 (JP) .................................. 2017-107400

(51) Int. Cl.
*D02G 3/44* (2006.01)
*A61F 13/00* (2006.01)
(Continued)

(52) U.S. Cl.
CPC .... *A61F 13/00063* (2013.01); *A61F 13/0243* (2013.01); *A61F 13/8405* (2013.01); *B01J 20/262* (2013.01); *B01J 20/28023* (2013.01); *B05B 11/30* (2013.01); *B32B 5/24* (2013.01); *B65D 81/28* (2013.01); *B65D 83/28* (2013.01); *D02G 3/36* (2013.01); *D02G 3/441* (2013.01);
(Continued)

(58) Field of Classification Search
CPC ........ D02G 3/441; D02G 3/449; H01L 41/08; H01L 41/082
USPC ..... 310/311, 313 A, 357, 359, 800; 442/110, 442/117, 203, 286, 288, 301
See application file for complete search history.

(56) References Cited

U.S. PATENT DOCUMENTS

| 5,869,189 A * | 2/1999 | Hagood, IV .......... H01L 41/082 310/357 |
| 2005/0000629 A1 * | 1/2005 | Bhardwaj ............... H01L 41/37 156/182 |

(Continued)

FOREIGN PATENT DOCUMENTS

| JP | H06205817 A | 7/1994 |
| JP | H0871124 A | 3/1996 |

(Continued)

OTHER PUBLICATIONS

International Search Report issued in PCT/JP2018/016534, dated Jul. 3, 2018.
(Continued)

*Primary Examiner* — Matthew D Matzek
(74) *Attorney, Agent, or Firm* — Arent Fox LLP

(57) ABSTRACT

A fabric that includes a first yarn and a second yarn which generate electric charges having different polarities with the application of external energy thereto. The fabric includes a low-density portion and a high-density portion having a lower porosity than the low-density portion.

20 Claims, 20 Drawing Sheets

(51) Int. Cl.
    *D03D 15/00*       (2006.01)
    *D04B 1/16*        (2006.01)
    *D04B 21/12*       (2006.01)
    *B65D 81/28*       (2006.01)
    *B01J 20/26*       (2006.01)
    *B01J 20/28*       (2006.01)
    *A61F 13/84*       (2006.01)
    *A61F 13/02*       (2006.01)
    *B65D 83/28*       (2006.01)
    *D02G 3/36*        (2006.01)
    *B32B 5/24*        (2006.01)
    *B05B 11/00*       (2006.01)

(52) U.S. Cl.
    CPC ............... *D03D 15/00* (2013.01); *D04B 1/16* (2013.01); *D04B 21/12* (2013.01); *A61F 2013/00646* (2013.01); *D03D 2700/0166* (2013.01); *D10B 2331/041* (2013.01); *D10B 2401/13* (2013.01); *D10B 2401/18* (2013.01); *D10B 2509/022* (2013.01); *D10B 2509/026* (2013.01)

(56) References Cited

U.S. PATENT DOCUMENTS

| | | | |
|---|---|---|---|
| 2010/0227521 A1* | 9/2010 | Whinnery | D03D 1/0088 442/189 |
| 2017/0029985 A1* | 2/2017 | Tajitsu | D03D 1/0088 |
| 2018/0108826 A1* | 4/2018 | Tajitsu | G06F 3/0414 |
| 2018/0315917 A1* | 11/2018 | Tanimoto | H01L 41/193 |
| 2019/0078239 A1 | 3/2019 | Ando et al. | |

FOREIGN PATENT DOCUMENTS

| | | |
|---|---|---|
| JP | 2002203996 A | 7/2002 |
| WO | 2015159832 A1 | 10/2015 |
| WO | 2017061209 A1 | 4/2017 |
| WO | 2017212523 A1 | 12/2017 |

OTHER PUBLICATIONS

Takaki, Koichi; "Agricultural and Food Processing Applications of High-Voltage and Plasma Technologies"; J. HTSJ, vol. 51, No. 216, Jul. 2012, pp. 64-69. (Translation of Section 5 p. 67 "Freshness retention and component extraction by high voltage").

* cited by examiner

FABRIC AND LIQUID ABSORBING ARTICLE

CROSS REFERENCE TO RELATED APPLICATIONS

The present application is a continuation of International application No. PCT/JP2018/016534, filed Apr. 24, 2018, which claims priority to Japanese Patent Application No. 2017-107400, filed May 31, 2017, the entire contents of each of which are incorporated herein by reference.

FIELD OF THE INVENTION

The present invention relates to a fabric having antibacterial properties and a liquid absorbing article containing the fabric.

BACKGROUND OF THE INVENTION

Conventionally, many proposals have been made in relation to antibacterial containers (see Patent Documents 1 and 2).

Patent Document 1: Japanese Patent Application Laid-Open No. 6-205817
Patent Document 2: Japanese Patent Application Laid-Open No. 8-71124

SUMMARY OF THE INVENTION

Both of the containers described in Patent Documents 1 and 2, however, are formed with an antibacterial substance contained in the wall of the container or the innermost layer thereof, which makes it difficult to manufacture the container. In addition, as a liquid or the like stored inside the container is expelled and therefore reduced in volume, the area of the container in contact with the liquid also is reduced, thereby making it difficult to efficiently exhibit antibacterial properties.

Therefore, an object of the present invention is to provide a fabric which efficiently exhibits antibacterial properties, and a liquid absorbing article containing the fabric.

An embodiment of the present invention includes a first yarn and a second yarn which generate electric charges having different polarities with the application of external energy thereto. The fabric includes a low-density portion and a high-density portion having a lower porosity than the low-density portion.

The fabric according to an embodiment of the present invention easily absorbs sweat, excrement or the like because of a large gap in the low-density portion. In contrast to this, the high-density portion generates a larger electric charge than the low-density portion because of a smaller gap in the high-density portion. Thus, the fabric according to an embodiment of the present invention quickly absorbs sweat, excrement or the like in the low-density portion, and uses an electric charge generated in the high-density portion to impart an antibacterial effect or a sterilizing effect to the sweat or excrement absorbed by the low-density portion. Therefore, the fabric according to an embodiment of the present invention can efficiently exhibit antibacterial properties.

A liquid absorbing article according to an embodiment of the present invention includes the fabric noted above and a liquid impermeable sheet attached to a principal surface of the fabric. Preferably, the liquid impermeable sheet is attached to a less irregular surface of opposed first and second principal surfaces.

The liquid absorbing article according to an embodiment of the present invention absorbs water or the like on the fabric side and prevents effusion of the absorbed water or the like to the outside on the impermeable sheet side. Therefore, the liquid absorbing article according to an embodiment of the present invention can exhibit antibacterial properties on the fabric without effusing the water or the like absorbed on the fabric side to the outside.

According to the present invention, a fabric which efficiently exhibit antibacterial properties and a liquid absorbing article containing the fabric can be achieved.

DETAILED DESCRIPTION OF THE INVENTION

Figure 1A:
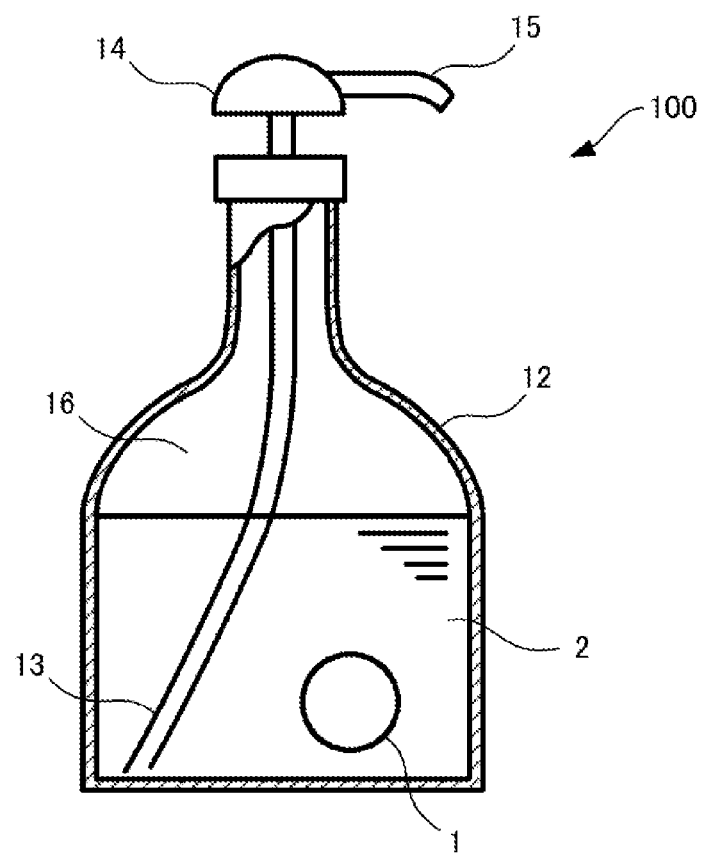
FIG. 1A is a view showing a container according to a first embodiment.
Figure 1B:
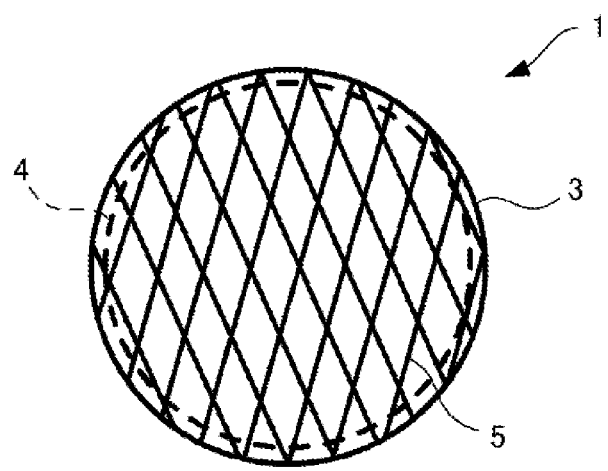
FIG. 1B is a view showing an antibacterial ball 1 according to the first embodiment.

FIG. 1A is a view showing a container 100 according to a first embodiment. FIG. 1B is a view showing an antibacterial ball 1 according to the first embodiment thereof. For convenience of explanation, a part of the container 100 is shown by a cross-sectional view in FIG. 1A. A molded member 4 is shown by dashed lines in FIG. 1B.

As shown in FIG. 1A, the container 100 includes a body 12, a hose 13, a pump 14, and a nozzle 15. The body 12 has an inner space 16 capable of storing a fluid 2. When a user operates to depress the pump 14, a pressure is applied to inside the container 100. The fluid 2 stored in the inner space 16 is sucked up with the hose 13 and discharged from the nozzle 15 to outside. The container 100 accommodates the antibacterial ball 1 in the inner space 16. The antibacterial ball 1 can be moved along with movement of the fluid 2 in the inner space 16. The pump 14 is exemplified which discharges the fluid 2 to outside from the container 100 by its depressing operation. It is, however, not limited to the depressing operation, and any operation by the user may be allowed as long as it moves the fluid 2 stored inside the container 100.

As shown in FIG. 1B, the antibacterial ball 1 includes a bag-shaped piezoelectric fiber net 3 and the molded member 4. The molded member 4 is covered with the bag-shaped piezoelectric fiber net 3. The piezoelectric fiber net 3 includes a plurality of piezoelectric fibers 5. The piezoelectric fiber net 3 is a mass of mesh-formed piezoelectric fibers 5, i.e., a knitted fabric. The mesh-formed mass is not limited to the knitted fabric, and the piezoelectric fibers 5 may be formed into a specified mass shape, including woven fabric or nonwoven fabric. The antibacterial ball 1 may have a shape that is easy to move in the fluid 2, such as a spherical shape, a disc shape or the like, the shape of which being established according to the intended usage.

Figure 2A:
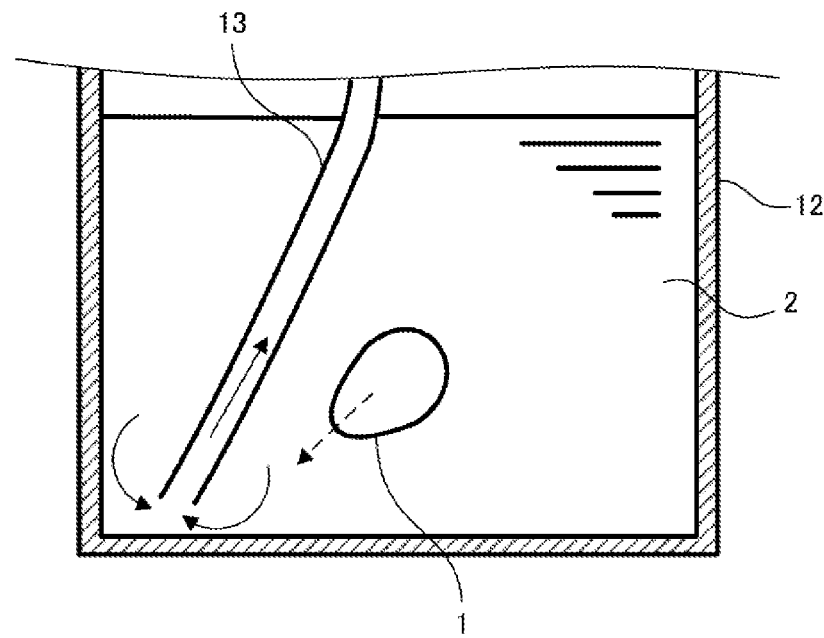
FIGS. 2A and 2B are views showing movement of the antibacterial ball 1 according to the first embodiment.
Figure 2B:
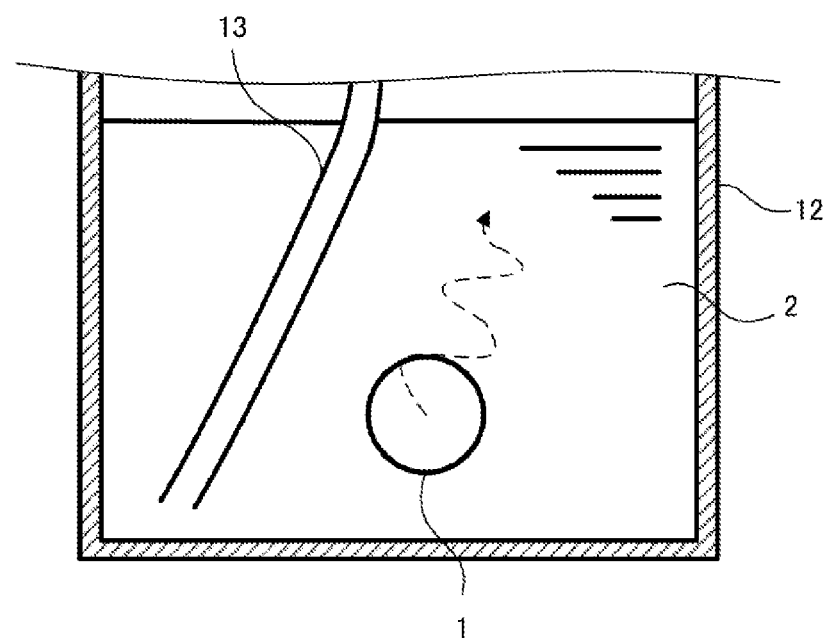

FIG. 2A is a view showing movement of the antibacterial ball 1 when the fluid 2 is discharged from the container 100. FIG. 2B is a view showing movement of the antibacterial ball 1 immediately after the fluid 2 is discharged from the container 100. As shown in FIG. 2A, when the fluid 2 is sucked up with the hose 13 and then discharged from the nozzle 15 to outside, the antibacterial ball 1 is sucked to the hose 13 together with the fluid 2. Immediately after the fluid 2 is discharged from the container 100, that is, when a user weakens a force applied to the pump 14, a force of the hose 13 which sucks the antibacterial ball 1 weakens. This releases the antibacterial ball 1 into the fluid 2. The piezoelectric fiber net 3 comes in contact with the fluid 2 and is deformed on the molded member 4 along with the movement of the fluid 2. When the piezoelectric fiber net 3 is deformed, an external force is applied to the piezoelectric fibers 5. The antibacterial ball 1 can also be moved in the fluid 2 by shaking the container 100 itself. In this case as well, an external force can be applied to the piezoelectric fibers 5.

The molded member 4 is preferably formed of inorganic material such as ceramic, or resin such as plastic. The molded member 4 may have any shape as long as the piezoelectric fiber net 3 covering its surface is affected by the movement of the fluid 2. The shape of the molded member 4 is, for example, a spherical shape, a rectangular parallelepiped shape, a disc shape, or the like. The antibacterial ball 1, that is, all of the piezoelectric fiber net 3 and the molded member 4, preferably has a specific gravity equal to or smaller than the fluid 2. This can prevent the antibacterial ball 1 from sinking into the fluid 2 so as not to be easily moved. The specific gravity of the antibacterial ball 1 is preferably set at a value such that the antibacterial ball 1 is present near a superficial layer of the fluid 2 in the container 100 while no force is applied thereto, so that the moving distance of the antibacterial ball 1 becomes long and the deformation of the piezoelectric fiber net 3 takes a long time. The piezoelectric fiber 5 will be described hereinbelow in detail.

Figure 3A:
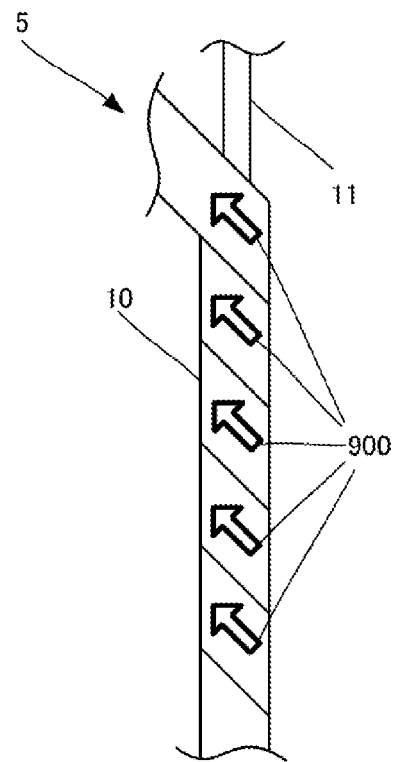
FIG. 3A is a view showing a configuration of a piezoelectric fiber 5 and FIG. 3B is a plan view of a piezoelectric film 10.
Figure 3B:
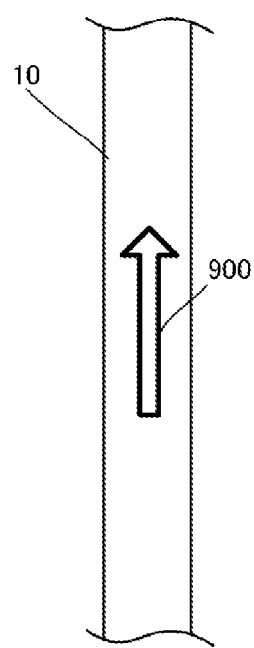

FIG. 3A is a partially exploded view showing a configuration of the piezoelectric fiber 5, and FIG. 3B is a plan view of a piezoelectric film 10. The piezoelectric fiber 5 generates an electric charge when an external force is applied thereto, that is, when energy is added from outside to deform the piezoelectric fiber 5.

The piezoelectric fiber 5 is made by winding the piezoelectric film 10 around a core yarn 11. The piezoelectric film 10 is an example of a piezoelectric body. The core yarn 11 is appropriately selected from natural fibers or chemical fibers. The natural fiber includes plant fiber, animal fiber, or semi-synthetic fiber such as polylactic acid or the like. Examples of the plant fiber include cotton or linen. When polylactic acid is used in the core yarn 11, the core yarn 11 does not need to be particularly a piezoelectric polylactic acid. As described later, when the polylactic acid is used in the piezoelectric film 10, the piezoelectric film 10 has a high affinity for the core yarn 11 because they are made of the same material. Examples of the chemical fiber include synthetic fiber, glass fiber, or carbon fiber. The chemical fiber is generally known to be sturdier than the natural fiber.

The core yarn 11 may be a conductive yarn having electrical conductivity. In the case of using a conductive yarn as the core yarn 11, when the piezoelectric properties of the piezoelectric fiber 5 are evaluated, an electric charge generated on the piezoelectric fiber 5 can be measured using an electrode formed on a part of the outer region of the piezoelectric fiber 5 and the core yarn 11. This allows the piezoelectric performance of the piezoelectric film 10 that is used on the piezoelectric fiber 5 to be checked. Further, the conductive yarns are short-circuited to each other to thereby clearly form a circuit among the yarns, so that an electric field generated between the surfaces of the yarns is remarkably increased. In the case of using an electrical conductor in the core yarn 11, when an electric current is passed through the core yarn 11, even a configuration in which an insulator other than the piezoelectric film 10 is wound around the core yarn 11, a thread which generates an electric charge by external energy can be achieved.

The core yarn 11, however, is not an essential component. Without the core yarn 11, it is possible to helically twist the piezoelectric film 10 to produce a piezoelectric yarn (twisted yarn). In the absence of the core yarn 11, the twisted yarn becomes hollow to improve heat retaining performance. Further, it is possible to increase the strength of the twisted yarn by impregnating the twisted yarn itself with a bonding agent. It is also possible to use a yarn obtained by twisting the piezoelectric film 10 into a two folded yarn or a twist yarn.

The piezoelectric film 10 is made of, for example, a piezoelectric polymer. Some of the piezoelectric films are pyroelectric and some are not. For example, polyvinylidene fluoride (PVDF) is pyroelectric and generates an electric charge due to temperature change. The piezoelectric body having pyroelectricity such as PVDF generates an electric charge on its surface due to heat energy on a human body.

Polylactic acid (PLA) is a piezoelectric film not having pyroelectricity. Polylactic acid is uniaxially stretched to have piezoelectric properties. Polylactic acid includes PLLA in which an L-form monomer is polymerized, and PDLA in which a D-form monomer is polymerized.

A chiral polymer such as polylactic acid has a spiral structure in its main chain. The chiral polymer has piezoelectric properties when molecules are oriented by uniaxially stretching. The piezoelectric film 10 made of uniaxially stretched polylactic acid has $d_{14}$ and $d_{25}$ tensor components as piezoelectric strain constants when the thickness direction of the piezoelectric film 10 is defined as a first axis, a stretching direction 900 thereof is defined as a third axis, and a direction perpendicular to both the first and third axes is defined as a second axis. Accordingly, polylactic acid generates an electric charge when a strain occurs in a direction at an angle of 45° to the uniaxially stretching direction.

Figure 4A:
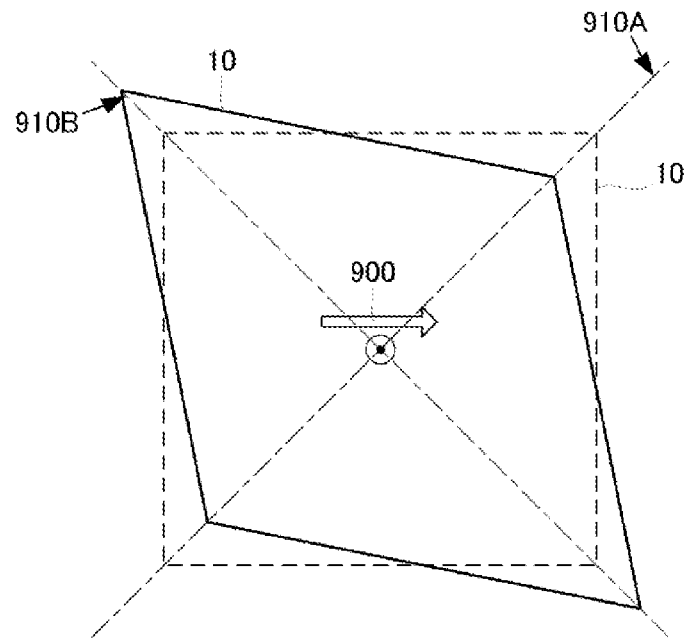
FIGS. 4A and 4B are views showing a relationship of a uniaxially stretching direction of polylactic acid, an electric field direction, and deformation of the piezoelectric film 10.
Figure 4B:
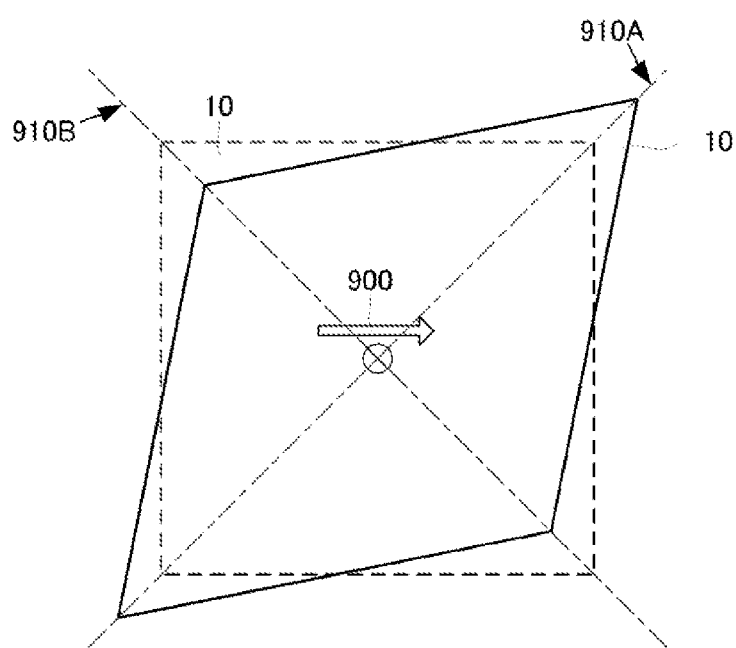
Figure 5:
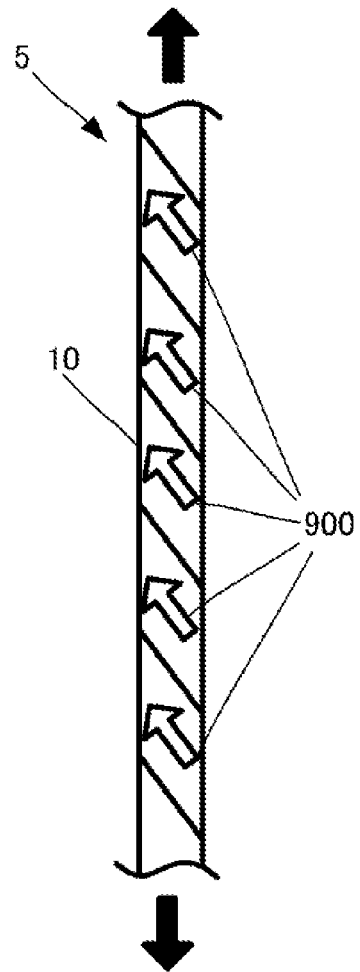
FIG. 5 is a view showing the piezoelectric fiber 5 when an external force is applied thereto.

FIGS. 4A and 4B are views showing a relationship of a uniaxially stretching direction of polylactic acid, an electric field direction, and deformation of the piezoelectric film 10. FIG. 5 is a view showing the piezoelectric fiber 5 when an external force is applied thereto. As shown in FIG. 4A, when the piezoelectric film 10 shrinks in a direction of a first diagonal line 910A and stretches in a direction of a second diagonal line 910B perpendicular to the first diagonal line 910A, an electric field is produced in a direction from the back side to the front side of the paper plane. That is, the piezoelectric film 10 generates a negative electric charge on the front side of the paper plane. As shown in FIG. 4B, even when the piezoelectric film 10 stretches in the first diagonal line 910A and shrinks in the second diagonal line 910B, an electric charge is generated, but the polarity is reversed, and an electric field is produced in a direction from the front side to the back side of the paper plane. That is, the piezoelectric film 10 generates a positive electric charge on the front side of the paper plane.

Since polylactic acid generates the piezoelectric properties due to molecular orientation processing by stretching, it does not need to be subjected to polling processing as do other piezoelectric polymers such as PVDF or piezoelectric ceramic. The uniaxially-stretched polylactic acid has a piezoelectric constant of approximately 5 to 30 pC/N, which is an extremely high piezoelectric constant among polymers. Further, the piezoelectric constant of the polylactic acid does not vary with time and is extremely stable.

The piezoelectric film 10 is produced by cutting a sheet of the uniaxially stretched polylactic acid as described above into a piece having, for example, a width of approximately 0.5 to 2 mm. As shown in FIG. 4B, the stretching direction 900 of the piezoelectric film 10 corresponds to the longitudinal direction. As shown in FIG. 5, the piezoelectric film 10 is made into the piezoelectric fiber 5 of a left-twisted yarn (hereinafter referred to as S yarn) in which the piezoelectric film 10 is twisted around the core yarn 11 to the left. The stretching direction 900 is angled at 45 degrees leftward with respect to the axial direction of the piezoelectric fiber 5. The S yarn is an example of the "first yarn" in the present invention.

Therefore, as shown in FIG. 5, when an external force is applied to the piezoelectric fiber 5, the piezoelectric film 10 becomes in the state as shown in FIG. 4A, which in turn generates a negative electric charge on a surface of the piezoelectric fiber 5. Though not shown in the Figure, in the case where the piezoelectric film 10 is made into the piezoelectric fiber 5 of a right-twisted yarn (hereinafter referred to as Z yarn) in which the piezoelectric film 10 is twisted around the core yarn 11 to the right, the application of an external force to the piezoelectric fiber 5 generates a positive electric charge on its surface. The Z yarn is an example of the "second yarn" in the present invention.

Thus, when an external force is applied, the piezoelectric fiber 5 generates a negative electric charge on its surface and a positive electric charge on the inside thereof. Therefore, the piezoelectric fiber 5 produces an electric field due to the potential difference generated by these electric charges. The electric field leaks to even adjacent spaces to form an electric field associated with other portions. When the potential produced in the piezoelectric fiber 5 comes close to an object having a given potential adjacent thereto, for example, a given potential (including a ground potential) of a human body or the like, an electric field is produced between the piezoelectric fiber 5 and the object. The piezoelectric fiber 5 may have a structure which produces an electric field due to a potential difference and may include either an S yarn or a Z yarn.

When the piezoelectric fibers 5 in the S yarn and the Z yarn are alternately knitted into the piezoelectric fiber net 3, positive and negative electric charges are generated from the S yarn and the Z yarn. Thus, a large electric field is produced between the S yarn and the Z yarn. This may cause an electric current to flow in a current path formed due to medium such as water present between the S and Z yarns, or in a circuit formed through a local phenomenon of microdischarge or the like.

Conventionally, there has been known that an electric field can inhibit the growth of bacteria (see, for example, "Agricultural and Food Processing Applications of High-Voltage and Plasma Technologies" written by Koichi TAKAKI, J. HTSJ, Vol. 51, No. 216). A potential difference which produces the electric field may cause an electric current to flow in a current path formed due to humidity or the like, or in a circuit formed through a local phenomenon of microdischarge or the like. The electric current may partially destroy cell membranes of bacteria to inhibit the growth of bacteria. The bacteria as used in this embodiment include germs, fungi, or microorganism such as mites, fleas, or the like.

The piezoelectric fibers 5 directly exert an antibacterial effect or a sterilizing effect due to the electric field formed near the piezoelectric fibers 5 or the electric field generated when the piezoelectric fibers 5 come close to an object having a given potential of a human body or the like. Alternatively, the piezoelectric fibers 5 allow an electric current to flow through moisture such as sweat, when they come close to an object having a given potential of another adjacent fiber, a human body, or the like. The piezoelectric fibers 5 may also directly exert an antibacterial effect or a sterilizing effect due to such an electric current. Alternatively, they may indirectly exert an antibacterial effect or a sterilizing effect due to active oxygen species which oxygen contained in moisture is converted into by the action of electric current or voltage, radical species generated by the interaction with an additive contained in the fibers or by catalysis, or other antibacterial chemical species (amine derivatives or the like). Or, stress environment caused by the presence of the electric field or current may produce oxygen radicals in cells of bacteria. This may allow the piezoelectric fibers 5 to indirectly exert an antibacterial effect or a sterilizing effect. As the radicals, superoxide anion radical (active oxygen) or hydroxy radical may be generated.

Therefore, the piezoelectric fibers 5 knitted in the piezoelectric fiber net 3 directly exert an antibacterial effect or a sterilizing effect due to the electric field produced when they are deformed along with the movement of the fluid 2. Thus, the antibacterial ball 1 which generates an electric charge can exert an antibacterial effect or a sterilizing effect when an external force is applied thereto. Therefore, it is possible to prevent microorganisms from propagating in the fluid 2 stored inside the container 100.

In the present embodiment, the piezoelectric film is described as an example of the piezoelectric body which forms the piezoelectric fiber 5. A piezoelectric monofilament yarn may, however, be used instead. The piezoelectric monofilament yarn is manufactured by any known method. The method that may be used include, for example, a method of extruding a piezoelectric polymer to form a fiber; a method of melt-spinning a piezoelectric polymer to form a fiber; a method of dry-spinning or wet-spinning a piezoelectric polymer to form a fiber; a method of electrostatic spinning to form a fiber; or the like. Also, when a yarn (covered yarn) made by twisting the piezoelectric monofilament yarn around the core yarn 11 is used as the piezoelectric fiber 5, a negative electric charge is generated on its surface by using the S yarn and a positive electric charge is generated on its surface by using the Z yarn. As the piezoelectric fiber 5, without using the core yarn 11, a twist yarn made by twisting the piezoelectric monofilament yarns alone may be used. Such twist yarn can be produced at low cost. In addition, as the piezoelectric fiber 5, a twist yarn made by twisting the piezoelectric monofilament yarn and an ordinary yarn (natural fiber such as cotton or linen, chemical fiber such as polyester, or the like) may be used. The containing of the ordinary yarn in the piezoelectric fiber 5 can improve surface smoothness and can prevent the container 100 from being damaged by contact.

Figure 6:
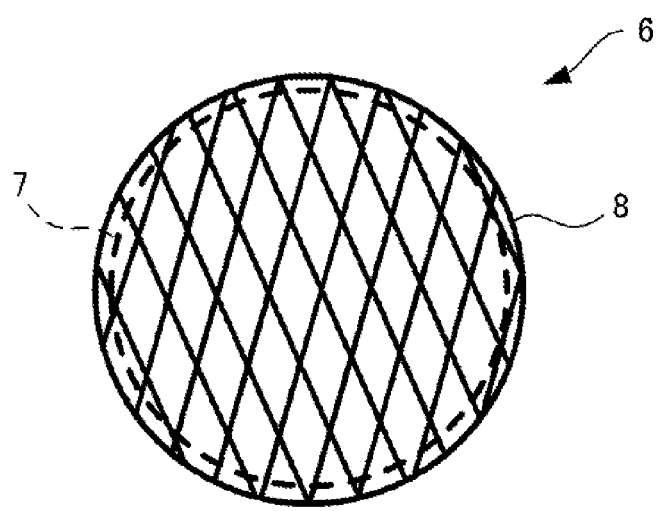
FIG. 6 is a view showing an antibacterial ball 6 according to a modification of the first embodiment.

FIG. 6 is a view showing an antibacterial ball 6 according to a modification of the first embodiment. The antibacterial ball 6 includes a piezoelectric portion 7 and a net 8. The piezoelectric portion 7 is covered with the net 8. The piezoelectric portion 7 is a spherical mass formed of the piezoelectric fibers 5. For example, a rounded knit having a spherical shape made of the piezoelectric fibers 5 may be used. The shape of the piezoelectric portion 7 is not limited to the spherical shape and can be formed into a required shape. The net 8 is formed of resin such as polyamide or the like in a mesh pattern. Since the net 8 has a mesh shape, the piezoelectric portion 7 arranged inside the net 8 can directly come in contact with the fluid 2 outside the net 8. Thus, the piezoelectric portion 7 is deformed by the movement of the fluid 2. Further, when the net 8 is formed of flexible material, the entire antibacterial ball 6 can be deformed as well as the piezoelectric portion 7. In this case as well, the piezoelectric portion 7 of the antibacterial ball 6 is deformed by the movement of the fluid 2. Therefore, the antibacterial ball 6 can exert an antibacterial effect or a sterilizing effect because the piezoelectric fibers 5 are deformed by deforming the piezoelectric portion 7 due to the movement of the fluid 2.

Figure 7:
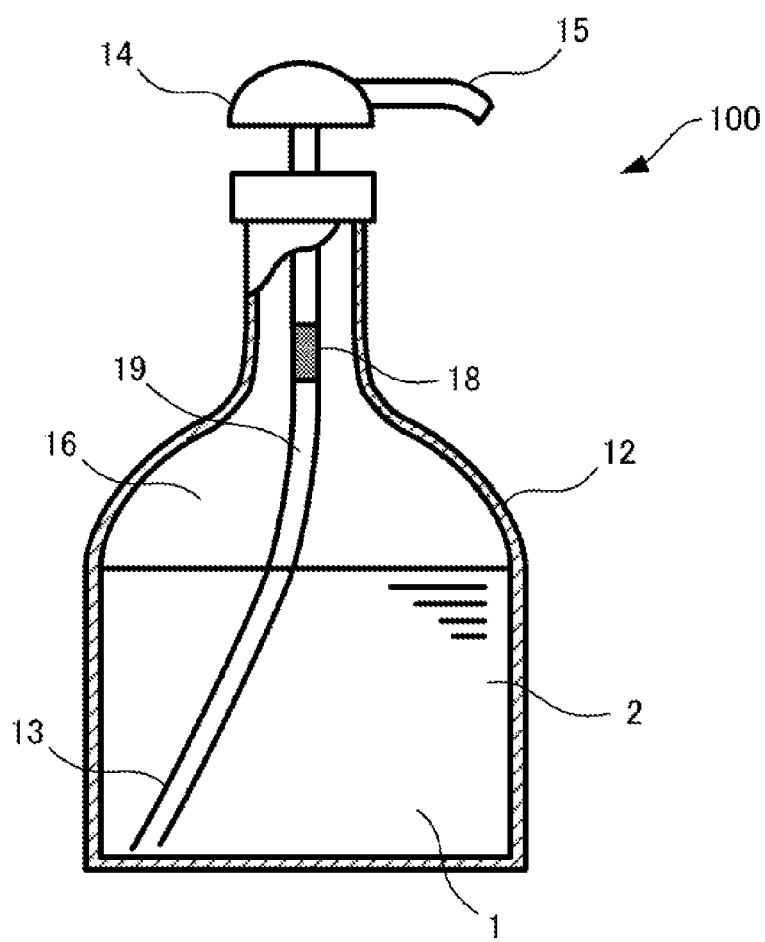
FIG. 7 is a view showing an antibacterial filter 18 according to a second embodiment.

FIG. 7 is a view showing an antibacterial filter 18 according to a second embodiment. For convenience of explanation, a part of the container 100 is shown by a cross-sectional view in FIG. 7.

As shown in FIG. 7, the antibacterial filter 18 according to the second embodiment is used integrally with the container 100 by being arranged in the hose 13. In the description of the antibacterial filter 18, no further discussion relating to the similar configuration to the antibacterial ball 1 will be provided.

The hose 13 has a flow passage 19 which connects between the inner space 16 and the container 100. That is, the hose 13 is a member which forms the flow passage 19 according to the present invention and the inner space of the hose 13 corresponds to the flow passage 19. The antibacterial filter 18 is a filter-like mass formed of the piezoelectric fibers 5. Examples thereof include knitted fabrics, woven fabrics, or nonwoven fabrics formed by compressing the piezoelectric fibers 5. The antibacterial filter 18 has a gap between the piezoelectric fibers 5. Therefore, the antibacterial filter 18 allows the fluid 2 to pass through in the hose 13.

When a user pushes the pump 14, the fluid 2 is sucked up with the hose 13 and discharged from the nozzle 15 to outside. The fluid 2 pressurizes the piezoelectric fibers 5 when passes through the gap between the piezoelectric fibers 5 in the antibacterial filter 18, so that the piezoelectric fibers 5 are deformed. Thus, the fluid 2 passes through the gap in the antibacterial filter 18, and at the same time, the piezoelectric fibers 5 generate electric charges. Therefore, the fluid 2 stored in the inner space 16 can be subjected to antibacterial treatment or sterilization when being discharged to outside. Since a preservative agent is not used, the fluid 2 can be safely subjected to antibacterial treatment or sterilization.

In the second embodiment, the antibacterial filter 18 is arranged inside the hose 13 of the container 100, but is not limited thereto. For example, the antibacterial filter 18 can be adapted to a liquid supply line such as a water pipe, a liquid supply line for circulating a liquid with a pump, a container having a flow passage which allows a liquid to flow in and out, or the like.

Figure 8A:
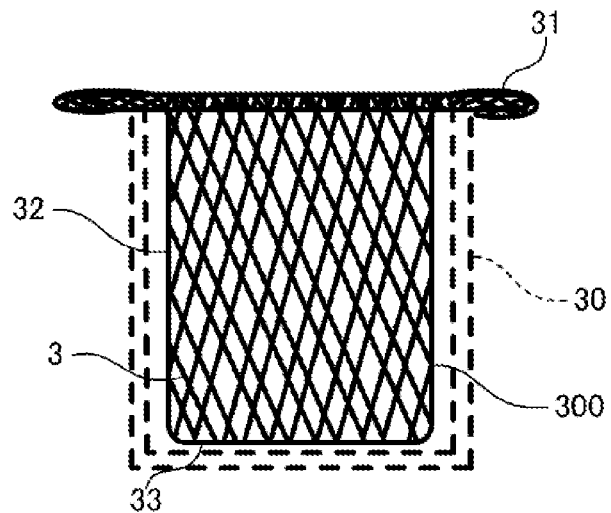
FIG. 8A is a view showing a slime removing net 300 according to a third embodiment.
Figure 8B:
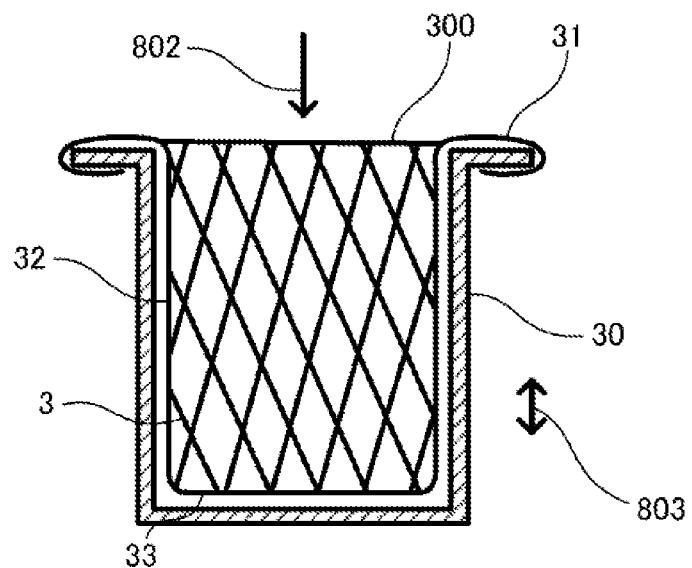
FIG. 8B is a view showing usage of the slime removing net 300 according to the third embodiment.
Figure 8C:
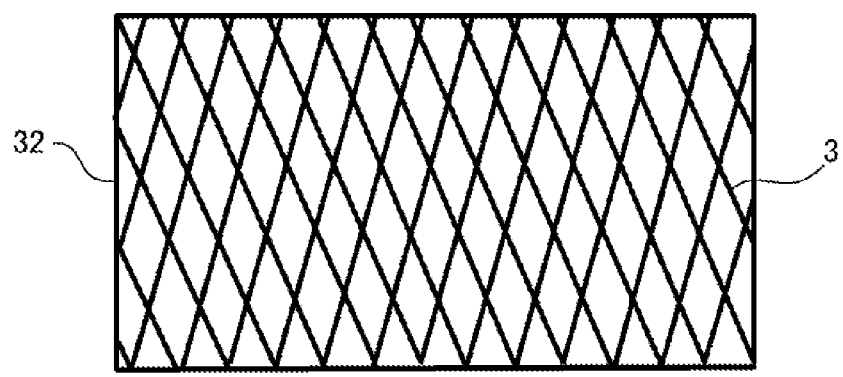
FIG. 8C is a developed plan view of a side section 32 of the slime removing net 300.

FIG. 8A is a view showing a slime removing net 300 according to a third embodiment. FIG. 8B is a view showing usage of the slime removing net 300 according to the third embodiment. FIG. 8C is a developed plan view of a side section 32 of the slime removing net 300. A strainer 30 is shown by dashed lines in FIG. 1A. In the third embodiment, no further discussion relating to the similar configuration to the above-mentioned embodiment will be provided.

As shown in FIG. 8A, the slime removing net 300 includes an end 31, a side section 32, and a bottom 33. The slime removing net 300 is mounted in the strainer 30 placed in a drain. For example, the slime removing net 300 is mounted so that the end 31 is fixed to the edge of the strainer 30 and the side section 32 is hung inside the strainer 30. The slime removing net 300 has a cylindrical shape with its upper portion being open and its lower portion being closed. The shape of the slime removing net 300 can be appropriately redesigned according to the configuration of the drain or the strainer 30. The slime removing net 300 can be applied to, for example, a triangular corner, other than the drain.

As shown in FIGS. 8A to 8C, the end 31 and the side section 32 of the slime removing net 300 are formed of the piezoelectric fiber net 3. The piezoelectric fiber net 3 includes a plurality of piezoelectric fibers 5 as in the first embodiment. Though not shown in the Figures, the bottom 33, as well as the side section 32, is also formed of the piezoelectric fiber net 3 and closes the lower portion of the slime removing net 300. The end 31, side section 32, and bottom 33 may be formed separately or continuously. The piezoelectric fiber net 3 is a knitted fabric in which the piezoelectric fibers 5 are formed in mesh shape. The piezoelectric fibers 5 include a Z yarn which generates a negative electric charge on its surface when an external force is applied, and an S yarn which generates a positive electric charge on its surface when an external force is applied. The piezoelectric fiber net 3 is not limited to the knitted fabric and may have the piezoelectric fibers 5 formed in a specified shape, including woven fabric or nonwoven fabric. In FIGS. 8A to 8C, the mesh size is not limited thereto, and may be made as fine as needed for the particular application of the slime removing net 300.

When water, drainage or the like flows to the drain, the water flows into the slime removing net 300 in the direction of an arrow 802. In the present embodiment, the water, drainage or the like flowing into the drain is an example of the "fluid". Along with the movement of the flowing water, the slime removing net 300 vibrates in the vertical direction (arrow 803) and the piezoelectric fibers 5 are then deformed. The vibration applies an external force to the Z yarn and the S yarn of the piezoelectric fibers 5, leading to generation of a negative or positive electric charge. Thus, the slime removing net 300 generates a negative or positive electric charge, so that the strainer 30 positioned therearound can be subjected to antibacterial treatment or sterilization. In addition, the slime removing net 300 can be safely handled by even a person having an allergy or sensitive skin because it does not use an antimicrobial agent, a germicide or the like. Further, the slime removing net 300 can prevent in advance soil contamination or the like caused by leakage of chemical substances such as a preservative agent into the drainage.

Figure 9A:
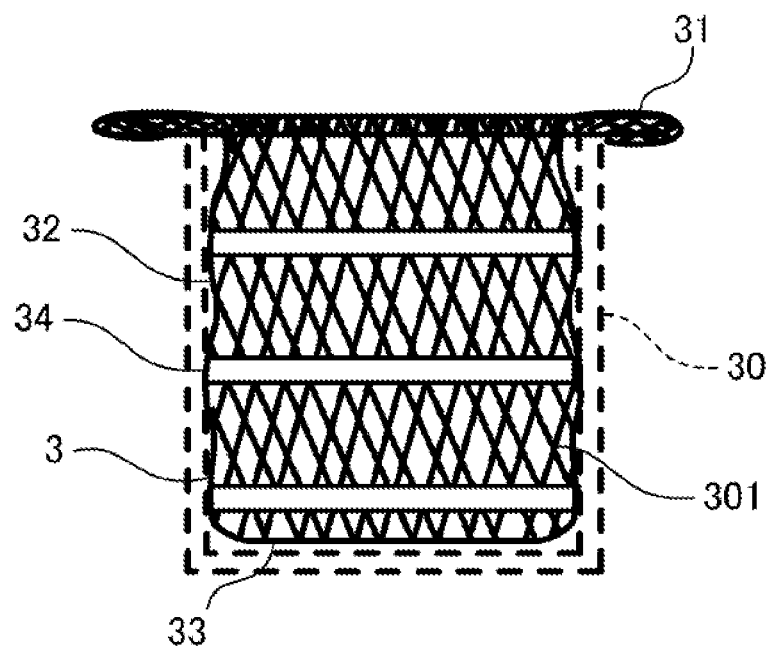
FIG. 9A is a view showing a slime removing net 301 according to a modification of the third embodiment.

FIG. 9A is a view showing a slime removing net 301 according to a modification of the third embodiment. The slime removing net 301 includes a wire 34. The wire 34 presses the side section 32 against outside, or the strainer 30. Thus, the slime removing net 301 can generate a negative or positive electric charge at a position closer to the strainer 30, so that it can further enhance an antibacterial effect or a sterilizing effect. Further, the presence of the wire 34 can maintain the cylindrical shape of the slime removing net 301 even though the piezoelectric fiber net 3 is formed of shrinkable material. This prevents the side section 32 from failing to normally vibrate due to shrinkage in the vertical direction, and also brings the side section 32 closer to the strainer 30, so that the slime removing net 301 can further enhance an antibacterial effect or a sterilizing effect.

Figure 9B:
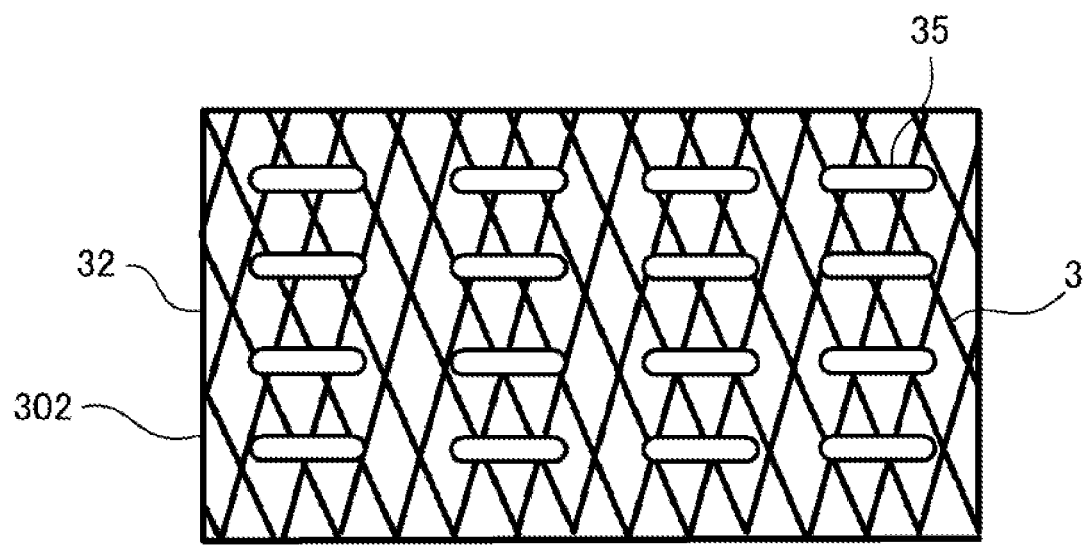
FIG. 9B is a view showing a slime removing net 302 according to a modification of the third embodiment.

FIG. 9B is a view showing a slime removing net 302 according to a modification of the third embodiment. The side section 32 of the slime removing net 302 includes a slit 35. One or a plurality of slits 35 is/are provided. The slits 35 are provided at regular intervals, including, for example, a plurality of slits provided in a peripheral direction of the side section 32, and a plurality of slits provided in the vertical direction of the side section 32. The slits 35 are preferably formed in parallel to each other in the peripheral direction of the slime removing net 302. Thus, a force of water flowing in the gravity direction parallel to an axial direction of the slime removing net 302 is efficiently applied to the slits 35. Therefore, providing the slits 35 can increase the deformation amount of the slime removing net 302 due to water.

When water is flown into the slime removing net 302, water flows along the inside of the slime removing net 302. At this time, while water is stored inside the slime removing net 302, some of the stored water is discharged outside through the slits 35 of the slime removing net 302 or the gaps between the piezoelectric fibers 5 of the piezoelectric fiber net 3. As the amount of water stored inside the slime removing net 302 increases, the slime removing net 302 is drawn downward. This deforms the piezoelectric fibers 5 of the piezoelectric fiber net 3, thereby generating an electric charge. In addition, the slits 35 are also vertically drawn downward, so that the opening of the slits 35 becomes large. Therefore, a more amount of water is externally flown out of the slime removing net 302 through the slits 35. As the amount of water stored inside the slime removing net 302 decreases, the drawn force applied to the slime removing net 302 weakens, so that the slime removing net 302 shrinks upward to return to its original shape. Therefore, providing the slits 35 can further increase the vibration of the slime removing net 302. In particular, in the case where the slime removing net 302 is a knitted fabric of the piezoelectric fibers 5, the vibration of the slime removing net 302 can be effectively increased. That is, in the case where the slime removing net 302 is a knitted fabric of the piezoelectric fibers 5, the gaps between the piezoelectric fibers 5 are small. Therefore, although the movement of the piezoelectric fibers 5 themselves is small, the slits 35 allow the slime removing net 302 to be largely deformed due to the outflow of water, so that the movement of the piezoelectric fibers 5 can be increased. Since water is flown out from the slits 35, the piezoelectric fiber net 3 can avoid the application of more than required force.

Figure 10A:
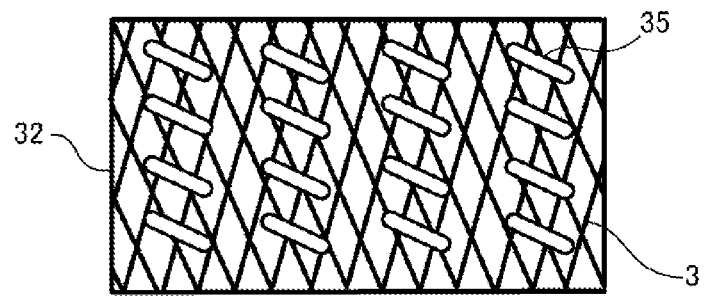
FIGS. 10A to 10D are views showing another embodiment of the slime removing net 302 according to the modification of the third embodiment.
Figure 10B:
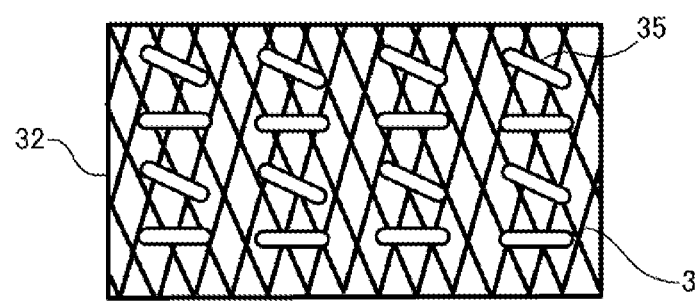
Figure 10C:
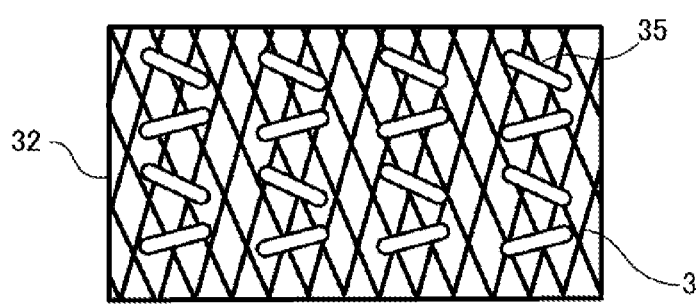

FIGS. 10A to 10D are views showing another embodiment of the slime removing net 302 according to the modification of the third embodiment. As shown in FIGS. 10A to 10C, the slits 35 may not necessarily be formed horizontally in the peripheral direction. For example, as shown in FIG. 10A, the slits 35 may be inclined at a predetermined angle relative to the horizontal direction in the peripheral direction. As shown in FIG. 10B, some of the slits 35 may be horizontally provided in the peripheral direction and the other slits may be inclined at a predetermined angle relative to the horizontal direction in the peripheral direction. As shown in FIG. 10C, the slits 35 are inclined at several angles relative to the horizontal direction in the peripheral direction.

Figure 10D:
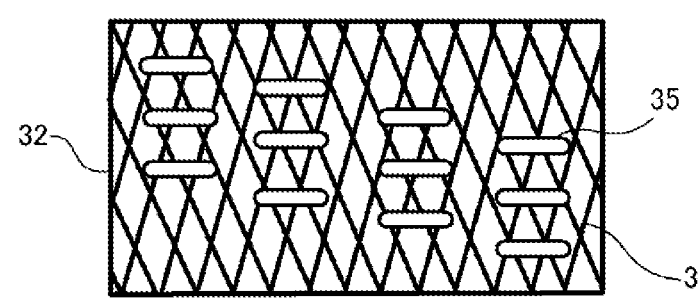

Further, as shown in FIG. 10D, the slits 35 may be provided in the side section 32 in the peripheral direction with two or more slits 35 being gradually shifted in the vertical direction. Therefore, the side section 32 includes a portion having many slits 35 formed and a portion having a few slits 35 formed. In the portion having many slits 35 formed, the movement of the piezoelectric fibers 5 becomes larger than the other portion. Thus, a portion where the movement of the piezoelectric fibers 5 is large and a portion where it is not can be provided according to the use state of the slime removing net 302.

Figure 11A:
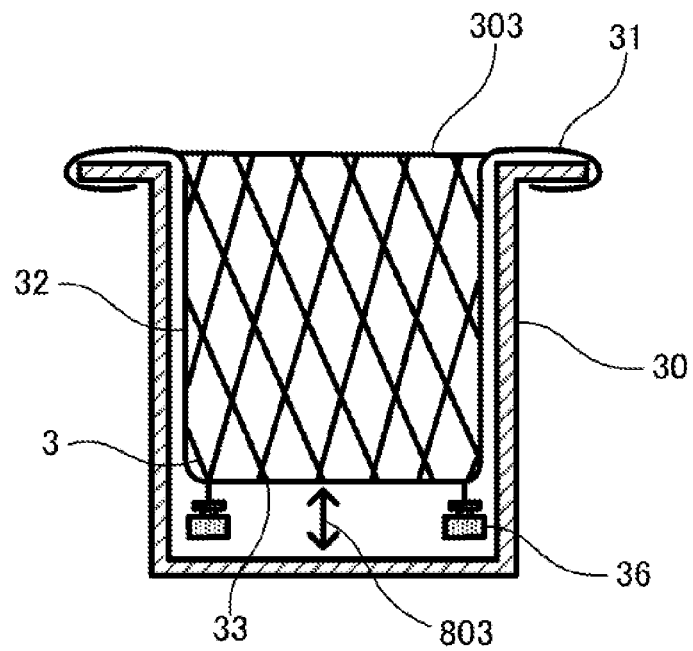
FIG. 11A is a view showing a slime removing net 303 according to a modification of the third embodiment.
Figure 11B:
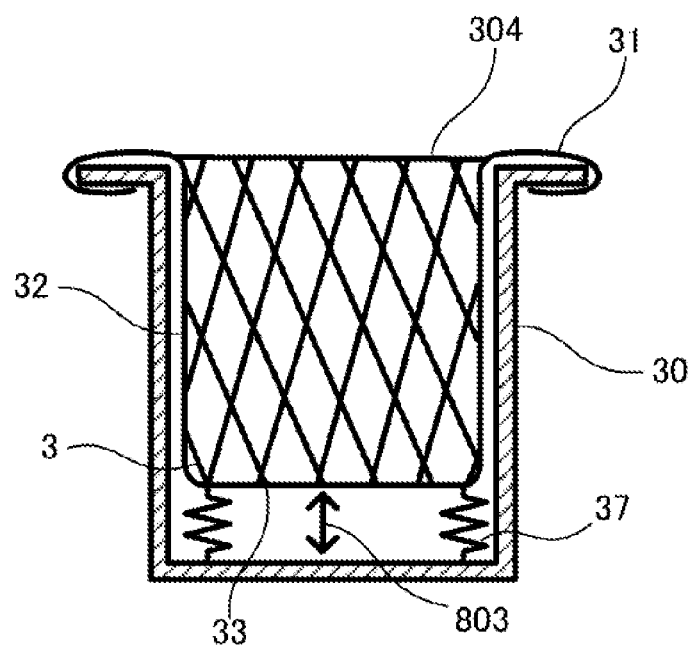
FIG. 11B is a view showing a slime removing net 304 according to a modification of the third embodiment.

FIG. 11A is a view showing a slime removing net 303 according to a modification of the third embodiment. FIG. 11B is a view showing a slime removing net 304 according to a modification of the third embodiment.

As shown in FIG. 11A, the slime removing net 303 includes a weight 36 on the bottom 33. The slime removing net 303 is drawn downward by the weight 36 even without water. For this reason, even though the piezoelectric fiber net 3 which forms the side section 32 of the slime removing net 303 is formed of shrinkable material, the cylindrical shape of the slime removing net 303 can be maintained. This prevents the side section 32 from failing to normally vibrate due to shrinkage in the vertical direction (arrow 803), and also brings the side section 32 closer to the strainer 30, so that the slime removing net 303 can further enhance an antibacterial effect or a sterilizing effect when vibrated.

As shown in FIG. 11B, the slime removing net 304 includes a spring 37 on the bottom 33. The slime removing net 304 is drawn downward by the spring 37 even without water. For this reason, even though the piezoelectric fiber net 3 which forms the side section 32 of the slime removing net 304 is formed of shrinkable material, the cylindrical shape of the slime removing net 304 can be maintained. This prevents the side section 32 from failing to normally vibrate due to shrinkage in the vertical direction (arrow 803), and also brings the side section 32 closer to the strainer 30, so that the slime removing net 303 can further enhance an antibacterial effect or a sterilizing effect when vibrated. In the case where water is absent, and in the case where the slime removing net 304 is pushed back upward by the spring 37, the slime removing net 304 is prevented from being fully stretched out and can also be largely vibrated along with the vibration of the spring 37.

Figure 12A:
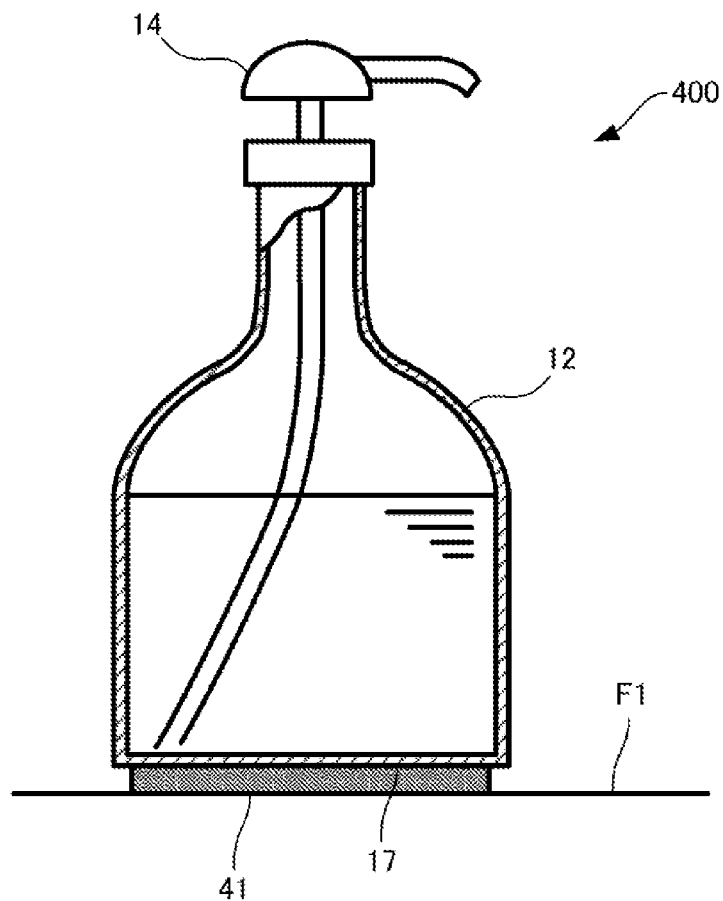
FIG. 12A is a view showing a container 400 according to a fourth embodiment.
Figure 12B:
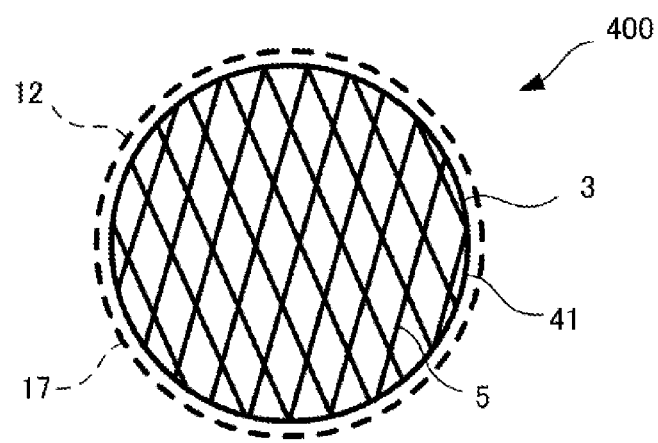
FIG. 12B is a view showing an antibacterial sheet 41 according to the fourth embodiment.

FIG. 12A is a view showing a container 400 according to a fourth embodiment. FIG. 12B is a bottom view of the container 400 showing an antibacterial sheet 41 according to the fourth embodiment. For convenience of explanation, a part of the container 400 is shown by a cross-sectional view in FIG. 12A. The body 12 is shown by dashed lines in FIG. 12B.

As shown in FIG. 12A, the container 400 is placed on a floor F1. Examples of the container 400 include bottles for detergents used in wet places such as a bathroom or a washroom. The container 400 according to the fourth embodiment includes an antibacterial sheet 41 on a bottom 17 of the body 12. Therefore, the antibacterial sheet 41 is positioned between the floor F1 and the bottom 17. The shape of the antibacterial sheet 41 can be appropriately redesigned according to the configuration of the container 400 or the arrangement place of the container 400.

As shown in FIG. 12B, the antibacterial sheet 41 may be attached to a portion of the bottom 17 of the container 400. The antibacterial sheet 41 preferably does not completely cover the bottom 17 of the container 400 so as to not lower the flexibility of the container 400. In the portion where the antibacterial sheet 41 is not attached to the bottom 17 of the container 400, a space is present between the floor F1 and the bottom 17. Air circulates in the space therebetween, and thereby good ventilation is achieved. This can suppress generation of mold, slime or the like on the bottom 17 of the container. The antibacterial sheet 41 may be attached to cover the entire bottom 17. Thus, the antibacterial properties can be imparted to the entire bottom 17. Further, the antibacterial sheet 41 may also be attached to cover the entire outside of the container 400. This can impart the antibacterial properties to the entire outside of the container 400.

The antibacterial sheet 41 includes the piezoelectric fiber net 3. The piezoelectric fiber net 3, as well as the slime removing net 300, includes a plurality of piezoelectric fibers 5. The inclusion of the plurality of piezoelectric fibers 5 causes irregularities on the surface of the antibacterial sheet 41 due to the fibers. This generates resistance to the floor F1 which is wet with water, so that the antibacterial sheet 41 can prevent slippage. Since slippage is prevented, the antibacterial sheet 41 steadily receives the force from the bottom 17. Further, the antibacterial sheet 41 is formed of material having lower rigidity than the container 400. Thus, when a force is applied to the container 400, the force can be easily transmitted to the antibacterial sheet 41 through the container 400.

The antibacterial sheet 41 is preferably detachable from the container 400. Thus, it can be attached to or detached as required. Examples of the antibacterial sheet 41 include a sheet or a seal having an adhesive portion. The antibacterial sheet 41 may be used by cutting a piece from an elongated sheet which is wound up, i.e., rolled, as required. The antibacterial sheet 41 may be formed in an appropriate size or shape. Thus, a user can select the size, the shape or the like of the antibacterial sheet 41 as required for use.

When a user pushes the pump 14, a force applied by the user transmits to the bottom 17. Even when the user moves the container 400, a force is applied to the bottom 17. The force provided to the bottom 17 transmits to the antibacterial sheet 41. The piezoelectric fibers 5 of the antibacterial sheet 41 thus deform, to thereby generate electric charges. The vibration applies an external force to the Z yarn and the S yarn of the piezoelectric fibers 5, leading to generation of a negative or positive electric charge. The antibacterial sheet 41 generates a negative or positive electric charge, so that the bottom 17 of the container 400 positioned therearound and the floor F1 around the antibacterial sheet 41 can be subjected to antibacterial treatment or sterilization. This can suppress generation of mold, slime or the like on the container 400 used in a wet place, so that the container 400 can be hygienically handled. Also, since a preservative agent is not used, the container 400 can be safely handled by even a person having an allergy or sensitive skin.

Figure 13:
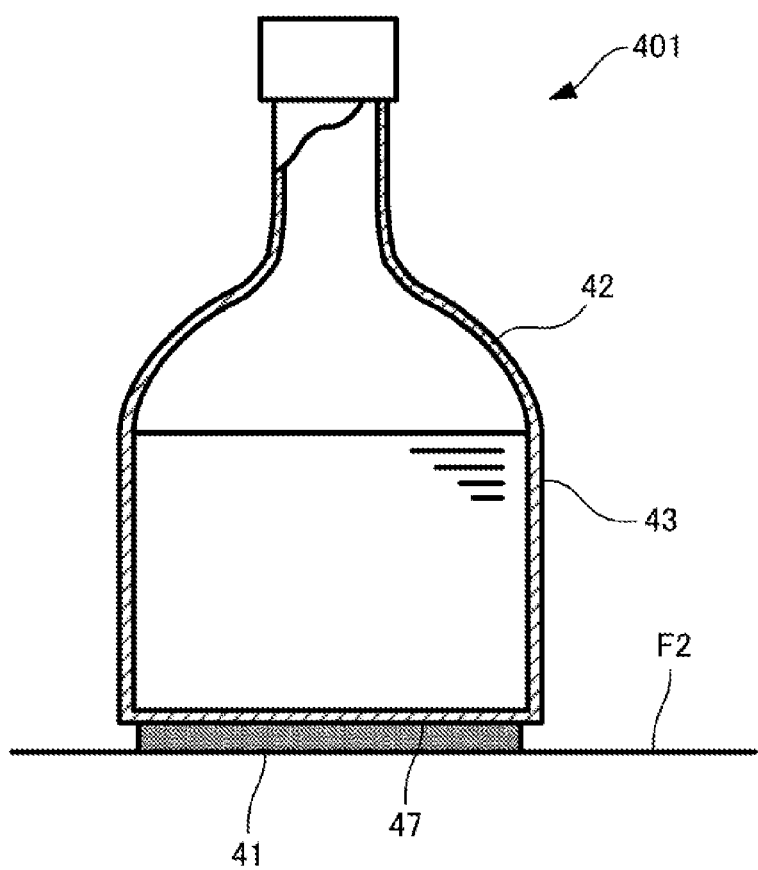
FIG. 13 is a view showing a container 401 according to a modification of the fourth embodiment.

FIG. 13 is a view showing a container 401 according to a modification of the fourth embodiment. For convenience of explanation, a part of the container 401 is shown by a cross-sectional view in FIG. 13.

As shown in FIG. 13, the container 401 is placed on a shelf F2 where dew condensation is liable to occur. Examples of the container 401 include bottles for mayonnaise or sauce stored in wet places susceptible to dew condensation such as a refrigerator. The container 401 includes the antibacterial sheet 41 on a bottom 47 of a body 42. Therefore, the antibacterial sheet 41 is positioned between the shelf F2 and the bottom 47. The shape of the antibacterial sheet 41 can be appropriately redesigned according to the configuration of the container 401 or the arrangement place of the container 401.

The antibacterial sheet 41 is formed of material having lower rigidity than the container 401. The container 401 is formed of flexible material. When a force is applied to a side section 43 of the container 401, the side section 43 of the container 401 is deformed. Along with the deformation of the side section 43, the bottom 47 is deformed. Along with the deformation of the bottom 47, the antibacterial sheet 41 is deformed.

For example, when a user holds the container 401, the container 401 deforms. The deformation of the container 401 is transmitted to the bottom 47. The force by deformation provided to the bottom 47 is transmitted to the antibacterial sheet 41. Even when the user places the container 400, a force is directly applied to the antibacterial sheet 41. The piezoelectric fibers 5 of the antibacterial sheet 41 thus deform, to thereby generate electric charges. Thus, the bottom 47 of the container 401 and the shelf F2 around the antibacterial sheet 41 can be subjected to antibacterial treatment or sterilization. This can suppress generation of mold, slime or the like on the container 401 used in wet places susceptible to dew condensation, so that the container 401 can be hygienically stored. Also, since a preservative agent is not used, the container 401 can be safely handled by even a person having an allergy or sensitive skin and can also be safely adapted to containers for food and drink.

Figure 14A:
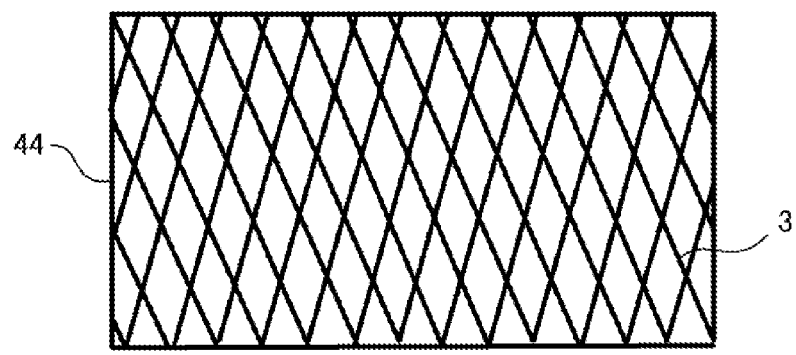
FIG. 14A is a view showing usage of an antibacterial sheet 44 according to a modification of the fourth embodiment.
Figure 14B:
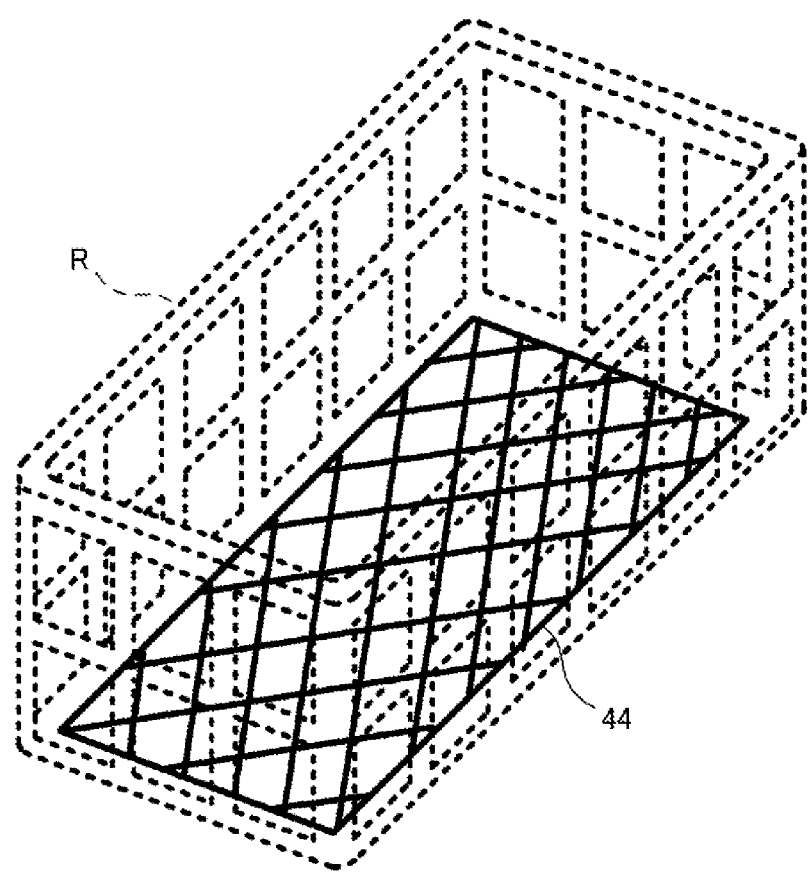
FIG. 14B is a view showing the antibacterial sheet 44.

FIG. 14A is a view showing an antibacterial sheet 44 according to a modification of the fourth embodiment. FIG. 14B is a view showing usage of the antibacterial sheet 44. In the description of the antibacterial sheet 44, no further discussion relating to the similar configuration to the antibacterial sheet 41 will be provided.

As shown in FIG. 14A, the antibacterial sheet 44 according to the modification of the fourth embodiment has a plate shape. The antibacterial sheet 44, as well as the antibacterial sheet 41, is formed of the piezoelectric fiber net 3. The piezoelectric fiber net 3 includes a plurality of piezoelectric fibers 5 as in the first embodiment.

As shown in FIG. 14B, the antibacterial sheet 44 is placed inside a rack R. The rack R that may be used include a basket-like container for holding a detergent bottle or the like used in a washroom, a kitchen, a bathroom or the like. The antibacterial sheet 44 may be uniform in the entire surface or may have a notch formed on a part thereof. For example, a portion surrounded by the notch is bent, and thereby the bent portion is hooked on the rack R, so that the antibacterial sheet 44 can be fixed. Alternatively, the antibacterial sheet 44 can be fixed to the rack R with another fastening tool or a bonding agent. Further, the antibacterial sheet 44 may be formed to be detachable to the rack R. For example, a surface of the antibacterial sheet 44 which comes in contact with the rack R may be formed as an adhesive or bonding surface.

When a user places a bottle (not shown) or the like in the rack R, the antibacterial sheet 44 is deformed by contact impact of the bottle. The deformation of the antibacterial sheet 44 leads to deformation of the piezoelectric fibers 5, to thereby generate electric charges. Thus, the rack R around the antibacterial sheet 44 and the bottle (not shown) can be subjected to antibacterial treatment or sterilization. This can suppress generation of mold, slime or the like on the rack R and the bottle (not shown) used in wet places, so that the rack R and the bottle can be hygienically used. Also, since a preservative agent is not used, the rack R and the bottle can be safely handled by even a person having an allergy or sensitive skin.

The antibacterial sheet 44 can be used in humid places without limitation to the rack R. For example, it can also be used in places susceptible to dew condensation, such as sashes of windows or doors, inside of a refrigerator, or the like.

Figure 15A:
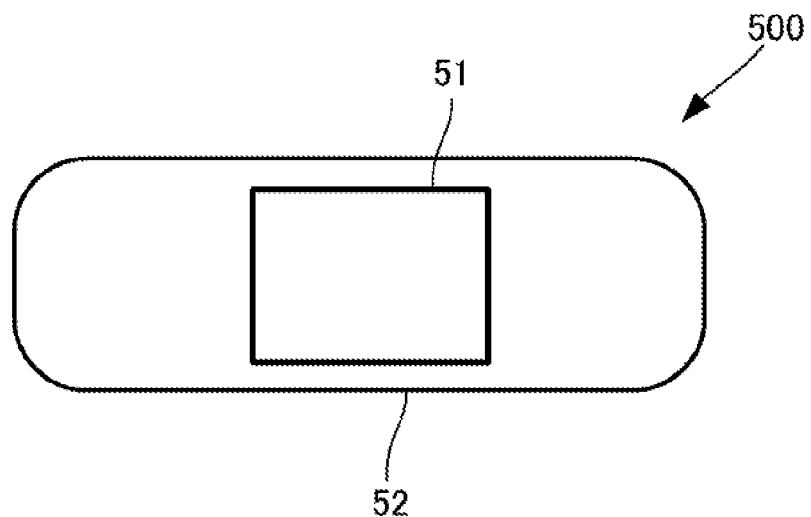
FIG. 15A is a plan view showing an adhesive plaster 500 according to a fifth embodiment.
Figure 15B:
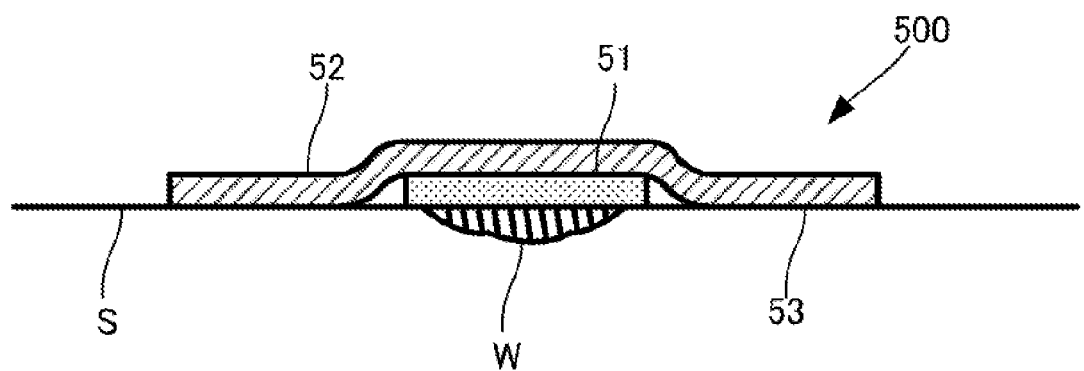
FIG. 15B is a schematic side view showing the use state of the adhesive plaster 500.

FIG. 15A is a plan view showing an adhesive plaster 500 according to a fifth embodiment. FIG. 15B is a schematic cross-sectional view showing the use of the adhesive plaster 500. FIG. 15A is a plan view viewed from a side where an antibacterial pad 51 is formed.

As shown in FIGS. 15A and 15B, the adhesive plaster 500 is used to protect a wound surface W of a skin S. The adhesive plaster 500 includes the antibacterial pad 51 and a protective sheet 52. The protective sheet 52 is formed of flexible material to have a sheet shape. One principal surface 53 of the protective sheet 52 is coated with an adhesive. The antibacterial pad 51 is placed in approximately the center of the principal surface 53 of the protective sheet 52. The adhesive plaster 500 is used by adhering to the skin S so that the antibacterial pad 51 comes in contact with the wound surface W. Thus, a part of the principal surface 53 of the protective sheet 52 can be adhered to the skin S with the adhesive. The shape or size of the antibacterial pad 51 and the protective sheet 52 can be redesigned according to the usage.

Figure 16:
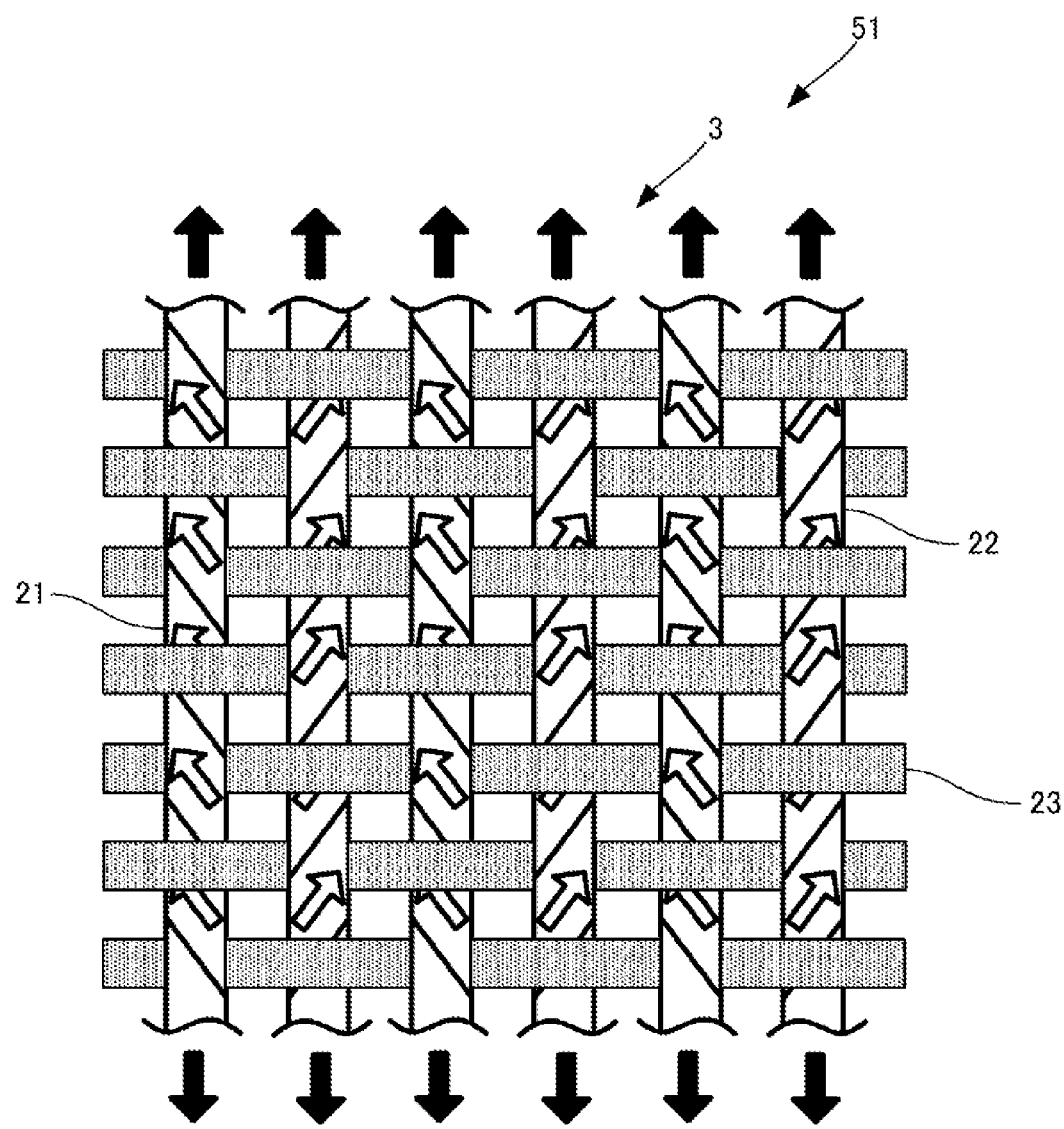
FIG. 16 is a schematic view showing an antibacterial pad 51.

FIG. 16 is a schematic view showing an antibacterial pad 51. As shown in FIG. 16, the antibacterial pad 51 has a plate shape. The antibacterial pad 51, as well as the antibacterial sheet 41, is formed of the piezoelectric fiber net 3. The piezoelectric fiber net 3 includes a plurality of piezoelectric fibers 5 and ordinary yarns 23 as in the first embodiment. The piezoelectric fibers 5 are used as warps and the ordinary yarns 23, as wefts to form a woven fabric. The ordinary yarns 23 may be used as warps and the piezoelectric fibers 5, as wefts to form a woven fabric. The ordinary yarn 23 that may be adopted includes, for example, cotton or linen. The antibacterial pad 51 may be formed by laminating a plurality of the piezoelectric fiber nets 3.

The piezoelectric fiber 5 includes an S yarn 21 and a Z yarn 22. The S yarns 21 and the Z yarns 22 are arranged side by side in parallel to each other in a longitudinal direction of the antibacterial pad 51. Thus, the piezoelectric fibers 5 are stretched along the longitudinal direction in which the antibacterial pad 51 largely moves, so that an electric charge can be efficiently generated. The S yarns 21 and the Z yarns 22 may be arranged side by side in a direction perpendicular to the longitudinal direction of the antibacterial pad 51. This case generates a smaller electric charge than the case where the S yarns 21 and the Z yarns 22 are arranged side by side in parallel to each other in a longitudinal direction of the antibacterial pad 51, so that it is applicable when the wound is mild. Further, the S yarns 21 and the Z yarns 22 may be arranged side by side in parallel to each other in the longitudinal direction of the antibacterial pad 51 and also side by side in a direction perpendicular to the longitudinal direction of the antibacterial pad 51. Thus, the S yarns 21 and the Z yarns 22 can efficiently generate electric charges without being affected by the case of being stretched in any direction. It is preferable that the S yarns 21 and the Z yarns 22 are alternately arranged. When an external force is applied to the piezoelectric fibers 5, the S yarn 21 generates a negative electric charge and the Z yarn 22 generates a positive electric charge. This produces a large potential difference between the S yarn 21 and the Z yarn 22 which are adjacent to each other. Further, the present embodiment exemplifies the plain weave as the piezoelectric fiber net 3. However, the weave is not limited thereto. For example, a knitted fabric or a nonwoven fabric can be adopted as the piezoelectric fiber net 3.

The adhesive plaster 500 is attached to the wound surface W so that the antibacterial pad 51 comes in contact with the wound surface W. When the wound surface W is not healed, body fluid such as blood or lymph oozes from the wound surface W. Thus, the body fluid is present on the wound surface W and between the piezoelectric fibers 5 of the antibacterial pad 51. The antibacterial pad 51 is deformed by the movement of the body fluid present on the wound surface W. In addition, the piezoelectric fibers 5 are more smoothly deformed due to the body fluid present therebetween. The deformation of the piezoelectric fibers 5 exerts an antibacterial effect or a sterilizing effect. When the wound surface W is not healed, the body fluid oozing from the wound surface W enables the antibacterial pad 51 to effectively provide antibacterial treatment or sterilization to the wound surface W.

After the adhesive plaster 500 is attached to the wound surface W, the wound surface W is healed over time. As the wound surface W is healed, the body fluid oozing from the wound surface W is reduced. The body fluid already oozed is dried and no longer flows. This reduces the body fluid present on the wound surface W and between the piezoelectric fibers 5 of the antibacterial pad 51. When the body fluid present on the wound surface W is reduced, the deformation of the antibacterial pad 51 becomes small. When the body fluid present between the piezoelectric fibers 5 reduces, the deformation of the piezoelectric fibers 5 decreases. Further, when the body fluid present between the piezoelectric fibers 5 is dried, the piezoelectric fibers 5 are fixed by the dried body fluid, so that they are no longer deformed. Since the deformation of the piezoelectric fibers 5 is suppressed, the antibacterial effect or the sterilizing effect is suppressed. For this reason, when the wound surface W is healed, the antibacterial effect or the sterilizing effect is not exerted more than necessary, which can prevent indigenous bacteria that are necessary for human body from being affected. Therefore, the adhesive plaster 500 can exert the antibacterial effect or the sterilizing effect as required. Therefore, there can be prevented suppuration of the wound surface W caused by, as in the case of using an antimicrobial agent, antibacterial performance degradation due to release of all the antimicrobial agent. The adhesive plaster 500 can be safely used for human bodies because of absence of an antimicrobial agent.

The piezoelectric fibers 5 directly exert an antibacterial effect or a sterilizing effect due to the electric field produced when they come close to an object having a given potential such as a human body or the like. Alternatively, the piezoelectric fibers 5 allow an electric current to flow through moisture such as sweat when they come close to an object having a given potential of a human body or the like. The piezoelectric fibers 5 may also directly exert an antibacterial effect or a sterilizing effect due to such an electric current. Alternatively, the piezoelectric fibers 5 may indirectly exert an antibacterial effect or a sterilizing effect due to radical species which oxygen contained in moisture is converted into by the action of electric current or voltage, radical species generated by the interaction with an additive contained in the fibers or catalysis, other antibacterial chemical species (amine derivatives or the like). As the radical species, superoxide anion radical (active oxygen) or hydroxyl radical may be generated. Thus, in the case where the antibacterial pad 51 exerts an antibacterial effect or a sterilizing effect, it inhibits growth of bacteria in and around an open sore, which can accelerate healing of the sore.

In the adhesive plaster 500, the antibacterial pad 51 is formed of the piezoelectric fiber net 3, and the protective sheet 52 may be formed of the piezoelectric fiber net 3. In this case, the protective sheet 52 is deformed by the movement of the skin S of a human. When the piezoelectric fibers 5 contained in the protective sheet 52 are deformed, an electric charge is generated in the protective sheet 52. This can exert an antibacterial effect or a sterilizing effect on the surface of the protective sheet 52, so that bacteria entered from outside of the adhesive plaster 500 can be subjected to antibacterial treatment or sterilization. The antibacterial pad 51 and the protective sheet 52 may be both formed of the piezoelectric fiber net 3. This can not only provide antibacterial treatment or sterilization on the wound surface W but, at the same time, can inhibit entry of bacteria from outside, so that the wound surface W can effectively be subjected to antibacterial treatment or sterilization.

Figure 17A:
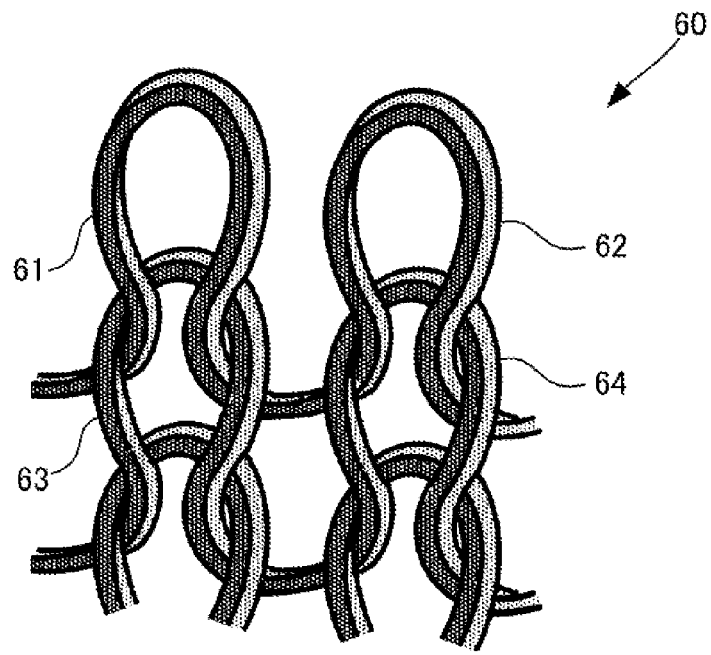
FIGS. 17A and 17B are views showing a piezoelectric fiber net 60 according to modifications of the fifth embodiment.
Figure 17B:
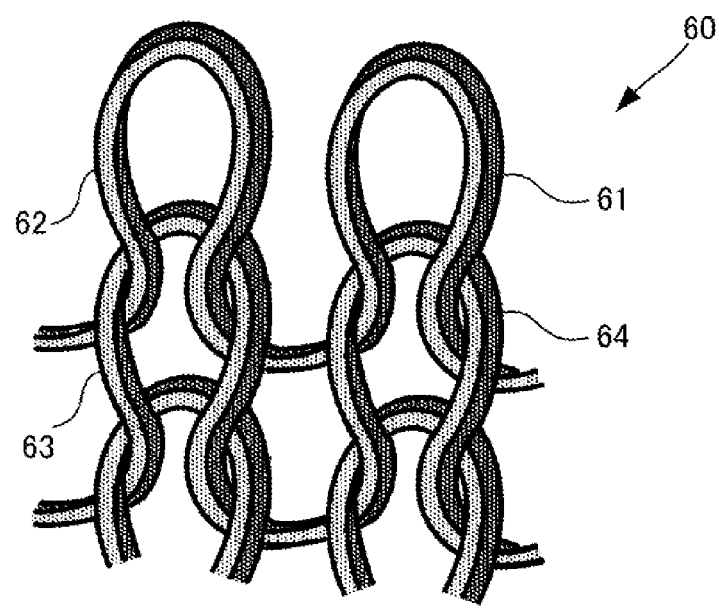

FIGS. 17A and 17B are views showing a piezoelectric fiber net 60 according to modifications of the fifth embodiment. The piezoelectric fiber net 60 is formed of a woven fabric. The piezoelectric fiber net 60 has a one-layer structure and may be a knitted fabric made by plating stitch using two knitting yarns, including a yarn constituting a charge generation portion 61 and a yarn constituting a non-charge generation portion 62. In the piezoelectric fiber net 60, a yarn extending on the front stitch side and a yarn extending on the back stitch side can be separately knitted with different kinds of yarns. In this case, as shown in FIG. 17A, a knitting yarn 63 forming the surface on the inside (on the front side of the paper plane) is the yarn constituting the charge generation portion 61. A knitting yarn 64 forming the surface on the outside (on the back side of the paper plane) is the yarn (cotton yarn, etc.) constituting the non-charge generation portion 62.

The antibacterial pad 51 can use the piezoelectric fiber net 60 as a surface of which the charge generation portion 61 comes in contact with the skin S. Thus, when the piezoelectric fiber net 60 is deformed, the charge generation portion 61 on the front side can be brought close to the skin S of a user. Therefore, when an electric charge is generated around the skin S, antibacterial treatment or sterilization can be efficiently provided. Further, the antibacterial pad 51 can use the piezoelectric fiber net 60 so that the non-charge generation portion 62 comes in contact with the skin S. Thus, when the piezoelectric fiber net 60 is deformed, the charge generation portion 61 on the back side can be positioned on the outside of the piezoelectric fiber net 60 of the user. Therefore, an electric charge is generated in a position near the outside of the adhesive plaster 500, thereby allowing bacteria entered from outside to be subjected to antibacterial treatment or sterilization.

The yarn constituting the charge generation portion 61 may include two kinds of piezoelectric yarns, an S yarn which generates a negative electric charge, and a Z yarn which generates a positive electric charge. In this case, two kinds of electric charges including a negative electric charge and a positive electric charge can be generated on a surface on the inside (on the front side of the paper plane). By adjusting the amount of the Z and S yarns, the ratio of the polarity of the electric charges generated according to the application can be adjusted. The yarn constituting the charge generation portion 61 may include a yarn (cotton yarn, etc.) which does not generate an electric charge, in addition to the Z yarn and the S yarn. In general, a piezoelectric yarn is worse in texture than cotton yarn or the like, so that when it touches the skin S, the skin S may be irritated. For this reason, when the yarn (cotton yarn, etc.) which does not generate an electric charge is partially used in the charge generation portion 61, the texture of the charge generation portion 61 is improved, and the irritation to the skin can be reduced. Alternatively, as shown in FIG. 17B, the knitting yarn 63 forming the surface on the inside (on the front side of the paper plane) can be the yarn constituting the non-charge generation portion 62 (cotton yarn, etc.) and the knitting yarn 64 forming the surface on the outside (on the back side of the paper plane) can be the yarn constituting the charge generation portion 61.

Figure 18A:
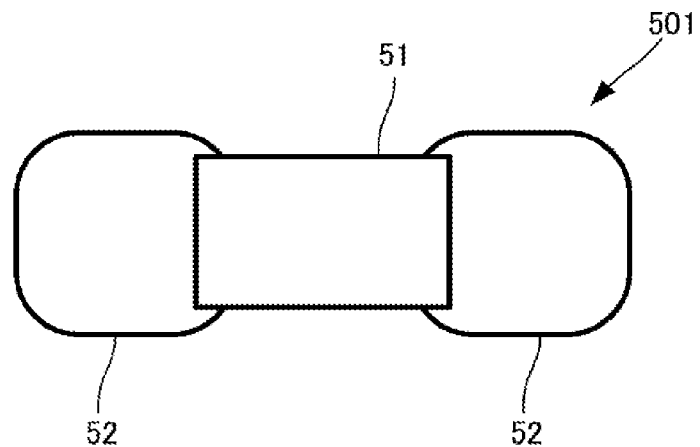
FIGS. 18A to 18C are views showing adhesive plasters 501 to 503 according to modifications of the fifth embodiment.
Figure 18B:
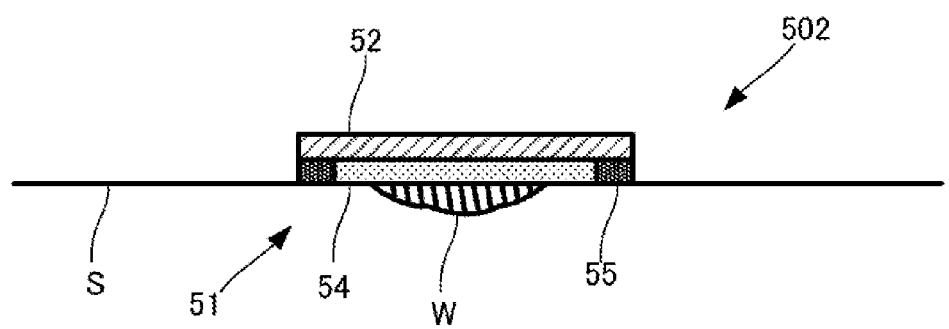
Figure 18C:
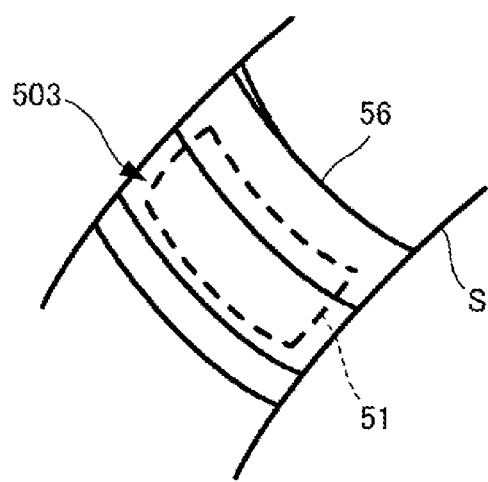

FIGS. 18A to 18C are views showing adhesive plasters 501, 502, and the antibacterial pad 51 according to modifications of the fifth embodiment. FIG. 18A is a plan view viewed from a side where the antibacterial pad 51 is formed. FIG. 18B is a schematic cross-sectional view of the adhesive plaster 502. FIG. 18C is a view showing the use state of the adhesive plaster 503, and the antibacterial pad 51 is shown by dashed lines. In the description of the adhesive plasters 501 to 503, no further discussion relating to the similar configuration to the adhesive plaster 500 will be provided.

As shown in FIG. 18A, the adhesive plaster 501 has a configuration in which the entire surface of the antibacterial pad 51 is not covered with the protective sheet 52. For this reason, a portion of the antibacterial pad 51 which is not adhered to the protective sheet 52 is configured with the antibacterial pad 51 alone. When the adhesive plaster 501 is attached to the wound surface W, the antibacterial pad 51 alone is present in a position opposed to the wound surface W. Thus, the antibacterial pad 51 can provide good ventilation because the protective sheet 52 does not cover the wound surface W. This can prevent the wound surface W from becoming stuffy and easily suppurated.

As shown in FIG. 18B, in the adhesive plaster 502, the antibacterial pad 51 includes an inner sheet 54 and a bonding portion 55. The bonding portion 55 is formed surrounding the inner sheet 54. The inner sheet 54 has the similar configuration to the antibacterial pad 51 of the adhesive plaster 500. The bonding portion 55 is the antibacterial pad 51 having adhesiveness or bonding properties. Examples of the bonding portion 55 include the antibacterial pad 51 coated with an adhesive or a bonding agent. Thus, the adhesive plaster 502 is attached to the skin S with the bonding portion 55 interposed therebetween. The protective sheet 52 is laminated so as to be overlapped with the inner sheet 54 and the bonding portion 55. Thus, the entire surface (inner sheet 54 and bonding portion 55) of the adhesive plaster 502 attached to the skin S has antibacterial or sterilizing properties, so that the adhesive plaster 502 can be formed small in size.

As shown in FIG. 18C, in the modification, the adhesive plaster 503 is the antibacterial pad 51, which is fixed so as to be wound around the skin S with a bandage 56. According to this, the adhesive plaster 503 does not use an adhesive or a bonding agent as the adhesive plaster 500 does. Therefore, a rash on the skin S due to a bonding agent or the bonding portion 55 can be prevented. The antibacterial pad 51 can also be fixed to the skin S using a mending tape or the like, instead of the bandage 56, according to the use state. The antibacterial pad 51 is handled separately from other members, so that the shape of the antibacterial pad 51 itself can be modified according to the wound W.

Figure 19A:
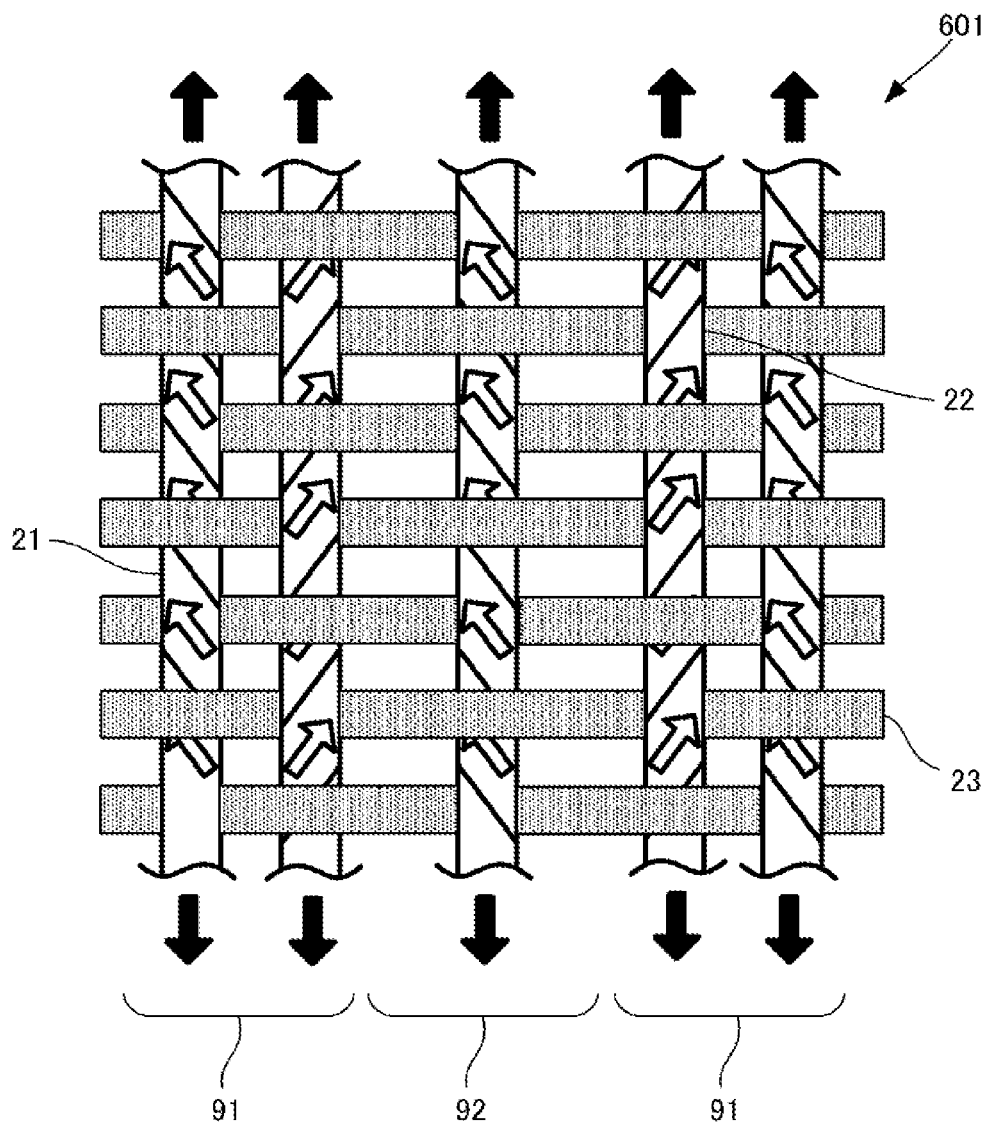
FIG. 19A is a schematic plan view showing an antibacterial sheet 601 according to a sixth embodiment.
Figure 19B:
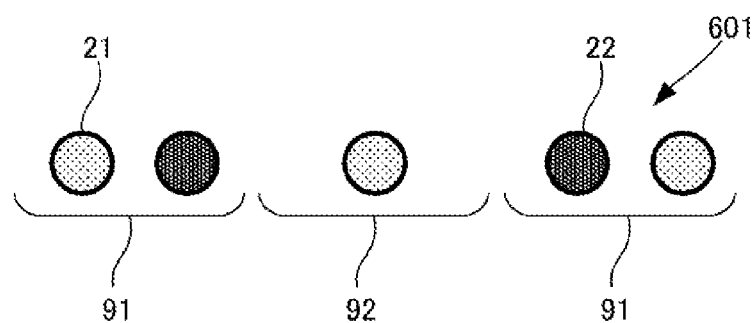
FIG. 19B is a schematic cross-sectional view showing the piezoelectric fibers 5 of the antibacterial sheet 601 according to the sixth embodiment.

FIG. 19A is a schematic plan view showing an antibacterial sheet 601 according to a sixth embodiment. FIG. 19B is a schematic cross-sectional view showing the piezoelectric fibers 5 of the antibacterial sheet 601 according to the sixth embodiment. The antibacterial sheet 601 is an example of a "fabric" in the present invention.

As shown in FIGS. 19A and 19B, the antibacterial sheet 601 includes the plurality of piezoelectric fibers 5 and the ordinary yarns 23 as in the fifth embodiment. The piezoelectric fibers 5 are used as warps and the ordinary yarns 23, as wefts to form a woven fabric. The ordinary yarns may be used as warps and the piezoelectric fibers 5, as wefts to form a woven fabric. The ordinary yarns 23 that may be used include, for example, natural fibers such as cotton and silk, or chemical fibers such as acryl and rayon in order to improve texture or elasticity. The antibacterial sheet 601 may also be used with a plurality of sheets being laminated.

The antibacterial sheet 601 includes the plurality of piezoelectric fibers 5. The piezoelectric fiber 5 includes the S yarn 21 and the Z yarn 22. In the case where the antibacterial sheet 601 has a longitudinal direction, it is preferable that the S yarns 21 and the Z yarns 22 are alternately arranged side by side in a direction perpendicular to the longitudinal direction of the antibacterial sheet 601. Thus, the piezoelectric fibers 5 are stretched along the longitudinal direction in which the antibacterial sheet 601 largely moves, so that an electric charge can be efficiently generated. It is preferable that the S yarns 21 and the Z yarns 22 are alternately arranged. When an external force is applied to the piezoelectric fibers 5, the S yarn 21 generates a negative electric charge and the Z yarn 22 generates a positive electric charge. This produces a large potential difference between the S yarn 21 and the Z yarn 22 which are adjacent to each other.

The antibacterial sheet 601 includes a high-density portion 91 having a high density of the piezoelectric fibers 5 and a low-density portion 92 having a low density of the piezoelectric fibers 5. In other words, the low-density portion 92 has a high porosity and the high-density portion 91 has a lower porosity than the low-density portion 92. In the high-density portion 91, the distance between the piezoelectric fibers 5 adjacent to each other is small, so that the generated electric charge becomes large. The high-density portion 91 and the low-density portion 92 are alternately arranged side by side. Thus, as shown in FIG. 19A, the antibacterial sheet 601 has a thick portion of the high-density portion 91 and a thin portion of the low-density portion 92 alternately formed in a cross-sectional view.

The antibacterial sheet 601 can be used as a material which comes in contact with a skin of a human or an animal, for example, diapers or sanitary articles. For example, a case where the antibacterial sheet 601 is used as diapers will be described. The shape of the antibacterial sheet 601 can be appropriately designed according to the configuration of the diaper or the arrangement place in the diaper. The diaper is required to be kept sanitary because it comes in contact with the skin S. The diaper is formed of flexible material. Thus, the diaper is deformed by the movement of the human or animal wearing the diaper.

When sweat, excrement or the like is adhered to the antibacterial sheet 601, the antibacterial sheet 601 absorbs the sweat, the excrement or the like inside. That is, sweat, excrement or the like is flown into the gaps formed by the piezoelectric fibers 5 or the ordinary yarns 23 and then retained there. At this time, the low-density portion 92 has large gaps formed by the piezoelectric fibers 5 or the ordinary yarns 23, so that it easily absorbs the sweat, the excrement or the like. In contrast to this, the high-density portion 91 has small gaps formed by the piezoelectric fibers 5 or the ordinary yarns 23, so that it is less likely to absorb the sweat, the excrement or the like than the low-density portion 92, but the generated electric charge is large as described above. Thus, sweat, excrement or the like can be quickly absorbed in the low-density portion 92, and the electric charges generated in the high-density portion 91 adjacent thereto can impart an antibacterial effect or a sterilizing effect to the sweat or the excrement absorbed by the low-density portion 92. Further, the plain weave is exemplified as the antibacterial sheet 601. However, the weave is not limited thereto. For example, a knitted fabric or a nonwoven fabric can be adopted as the antibacterial sheet 601. In the present invention, the term "fabric" includes woven fabrics, knitted fabrics, or nonwoven fabrics.

Figure 20A:
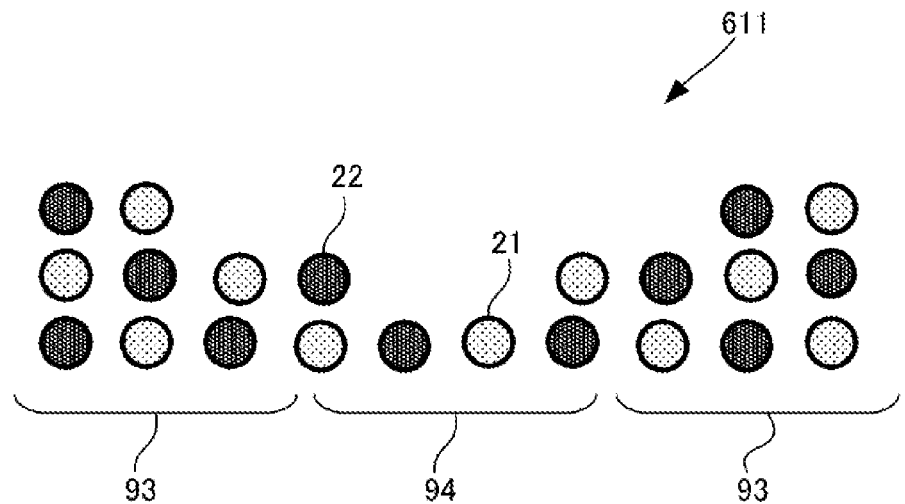
FIG. 20A is a schematic cross-sectional view showing an antibacterial sheet 611 according to a modification of the sixth embodiment.
Figure 20B:
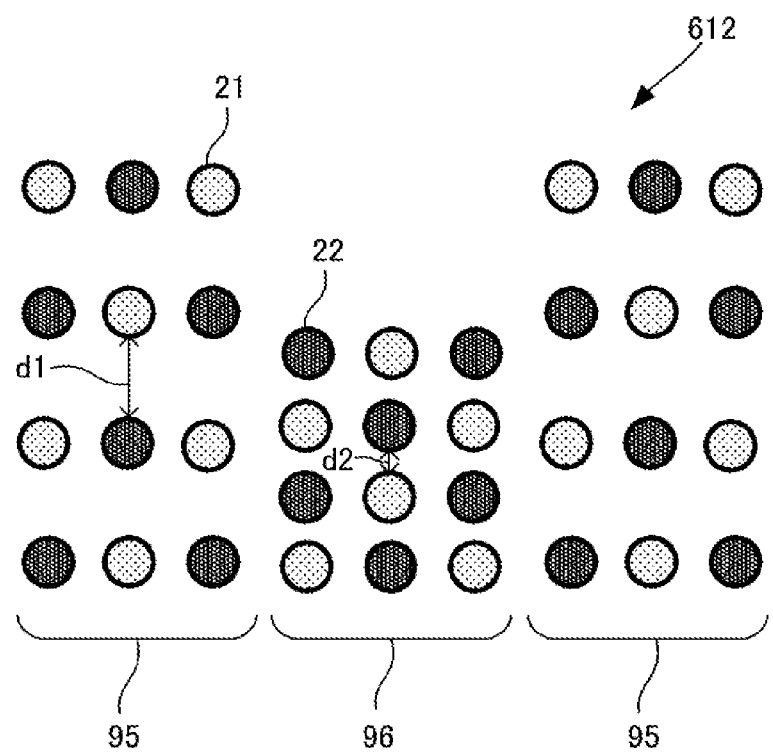
FIG. 20B is a schematic cross-sectional view showing an antibacterial sheet 612 according to a modification of the sixth embodiment.
Figure 20B:
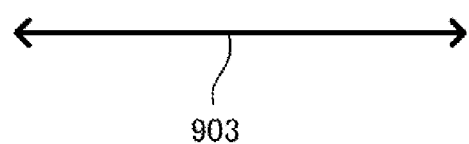
Figure 21A:
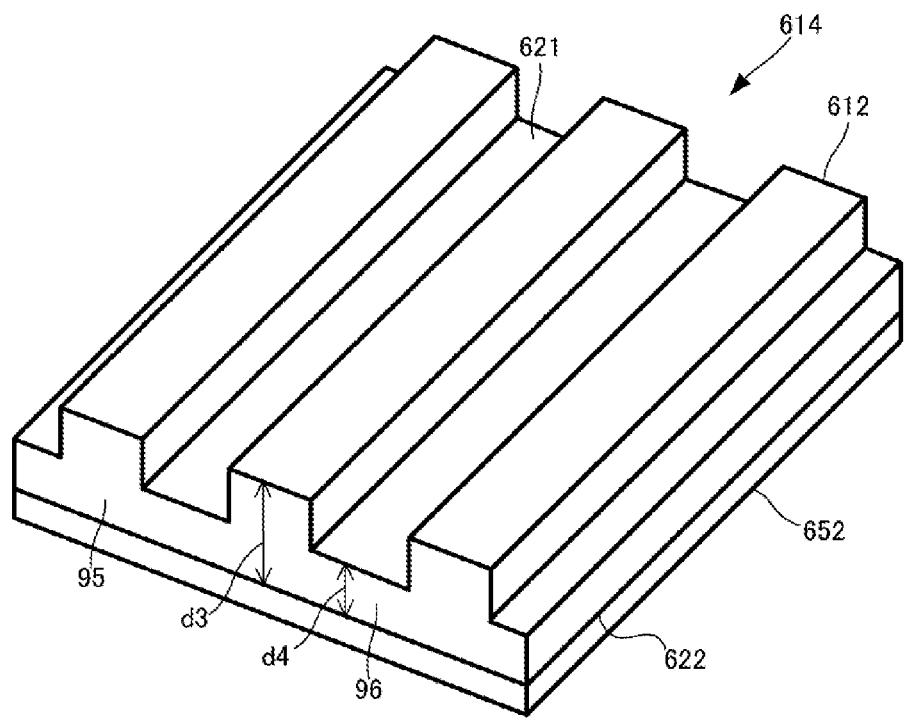
FIG. 21A is a schematic view showing the antibacterial sheet 612 according to a modification of the sixth embodiment.
Figure 21B:
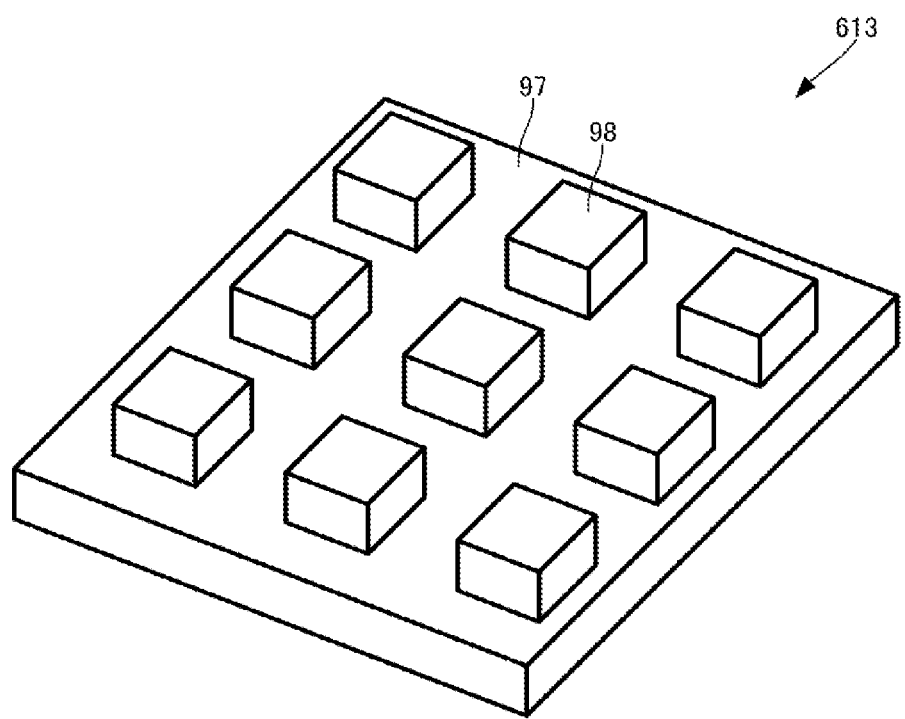
FIG. 21B is a schematic view showing an antibacterial sheet 613 according to a modification of the sixth embodiment.

FIG. 20A is a schematic cross-sectional view showing an antibacterial sheet 611 according to a modification of the sixth embodiment. FIG. 20B is a schematic cross-sectional view showing an antibacterial sheet 612 according to a modification of the sixth embodiment. FIG. 21A is a schematic view showing the antibacterial sheet 612 according to a modification of the sixth embodiment. FIG. 21B is a schematic view showing an antibacterial sheet 613 according to a modification of the sixth embodiment. FIGS. 20A and 20B show the S yarns 21 and the Z yarns 22 alone. The antibacterial sheets 612 and 613 are an example of a "fabric" in the present invention.

As shown in FIG. 20A, the antibacterial sheet 611 includes the S yarns 21 and the Z yarns 22, which are provided at regular intervals. In the antibacterial sheet 611, the S yarns 21 and the Z yarns 22 are laminated. The antibacterial sheet 611 includes a high stack portion 93 and a low stack portion 94. The high stack portion 93 has the S yarns 21 and the Z yarns 22 thickly laminated, and the low stack portion 94 has the S yarns 21 and the Z yarns 22 thinly laminated. The surface of the antibacterial sheet 611 becomes irregular because the high stack portion 93 and the low stack portion 94 are different in height. Thus, as in the antibacterial sheet 601, sweat or excrement is quickly absorbed in the low stack portion 94. Further, in the high stack portion 93 where the S yarns 21 and the Z yarns 22 are present in large number, the generated electric charge is large. Therefore, as in the antibacterial sheet 601, an antibacterial effect or a sterilizing effect can be imparted to the sweat, the excrement or the like absorbed in the antibacterial sheet 611. Since the antibacterial sheet 611 has the irregular surface, capillary action works, so that a recessed portion in the low stack portion 94 can quickly absorbs sweat, excrement or the like. This can further quickly impart an antibacterial effect or a sterilizing effect to the antibacterial sheet 611.

As shown in FIG. 20B, in the antibacterial sheet 612, the amount of the S yarns 21 and the Z yarns 22 laminated in the thick direction is approximately the same as that in any position in a direction 903 perpendicular to the S yarns 21 and the Z yarns 22. In a high-density portion 96, the S yarns 21 and the Z yarns 22 are densely laminated, while in a low-density portion 95, the S yarns 21 and the Z yarns 22 are coarsely laminated. In other words, a distance d1 between the S yarn 21 and the Z yarn 22 in the low-density portion 95 is larger than a distance d2 between the S yarn 21 and the Z yarn 22 in the high-density portion 96.

Since the high-density portion 96 has the S yarns 21 and the Z yarns 22 crowded, it is strong, excellent in durability, and keeps fluid between the S yarns 21 and the Z yarn 22. In addition, in the high-density portion 96, the distance between the S yarn 21 and the Z yarn 22 is close, so that a large electric charge can be generated. Therefore, in the high-density portion 96, the kept fluid can be efficiently subjected to antibacterial treatment or sterilization with the large electric charge.

In contrast to this, since the low-density portion 95 has the S yarns 21 and the Z yarns coarsely laminated, fluid such as sweat, excrement or the like in the gap can be efficiently flown into the side of the high-density portion 96. The low-density portion 95 is smaller than the high-density portion 96, but generates an electric charge, so that the fluid slightly adhered to the low-density portion 95 can be subjected to antibacterial treatment or sterilization. In addition, the low-density portion 95 is excellent in elasticity and is stretched by the movement of a human, so that a sense of discomfort during wearing can be alleviated.

The antibacterial sheet 612 has an irregular surface because the high-density portion 96 and the low-density portion 95 are different in height. Thus, as well as the antibacterial sheet 601, the antibacterial sheet 612 allows the sweat, the excrement or the like to be quickly flown into the high-density portion 96 through the low-density portion 95, so that it can efficiently impart the fluid to an antibacterial effect or a sterilizing effect.

When the antibacterial sheet 612 is viewed in cross section, the low-density portion 95 is preferably thicker than the high-density portion 96. The low-density portion 95 first touches a skin before the high-density portion 96, thereby allowing the antibacterial sheet 612 to efficiently let fluid such as sweat or excrement flow into the high-density portion 96. Further, since the high-density portion 96 can be kept apart from the skin, it is possible to reduce possibility that the fluid such as sweat or excrement absorbed in the high-density portion 96 directly touches the skin. As a result of this, the antibacterial sheet 612 can improve its texture.

The antibacterial sheet 612 can be relatively easily manufactured by forming a high-pressed portion and a low-pressed portion with a press machine or feeding raw material into a mold having an irregular shape. As shown in FIG. 21A, the high-density portion 96 and the low-density portion 95 are alternately formed in ridges. That is, the antibacterial sheet 612 includes a first principal surface 621 and a second principal surface 622 which is positioned opposite to the first principal surface 621. A distance d3 from the first principal surface 621 to the second principal surface 622 in the low-density portion 95 is larger than a distance d4 from the first principal surface 621 to the second principal surface 622 in the high-density portion 96. Thus, the surface of the high-density portion 96 is formed into groove, so that further water or the like is easily absorbed by the antibacterial sheet 612.

The antibacterial sheet 612 further has a liquid impermeable sheet 652. In other words, a sheet 614 includes an antibacterial sheet 612 and the sheet 652. The antibacterial sheet 612 is attached to the sheet 652 on the side of the second principal surface 622. That is, the sheet 652 is attached to the second principal surface 622 which is less irregular flat surface, of either the first principal surface 621 or the second principal surface 622. In the antibacterial sheet 612, the first principal surface 621 having irregularities absorbs water or the like, and the sheet 652 can prevent the absorbed water or the like from leaking outside. Therefore, the antibacterial sheet 612 can exhibit antibacterial properties on the side of the first principal surface 621 without effusing the water or the like absorbed from the side of the first principal surface 621 to the outside. The sheet 614 having the liquid impermeable sheet 652 is an example of the "liquid absorbing article" in the present invention.

As shown in FIG. 21B, the antibacterial sheet 613 has a high-density portion 97 and a low-density portion 98. The antibacterial sheet 613 is formed so that the high-density portion 96 and the low-density portion 95 are differently shaped when the antibacterial sheet 612 is formed. The shapes of the high-density portion 97 and the low-density portion 98 can be redesigned as required.

For example, a case where the antibacterial sheet is formed with two layers of a high-density portion and a low-density portion is included. In this case, the low-density portion may be arranged in spaced relation to a flat sheet of the high-density portion. For example, in the case of forming an antibacterial sheet like the antibacterial sheet 613 shown in FIG. 21B, the projected portions are the low-density portion 95. Thus, the low-density portion 95 alone is projected from the high-density portion 96, so that only the low-density portion 95 partially formed can touch the skin.

Finally, the present embodiments should therefore be considered in all respects as illustrative and not restrictive. The scope of the invention is given by the appended claims, rather than the preceding embodiments. Further, all variations and equivalents which fall within the range of the claims are intended to be embraced therein.

DESCRIPTION OF REFERENCE SYMBOLS 1, 6: Antibacterial ball
2: Fluid 3, 60: Piezoelectric fiber net
5: Piezoelectric fiber (electric charge generation yarn)
10: Piezoelectric film
18: Antibacterial filter
21: S yarn (first yarn)
22: Z yarn (second yarn)
35: Slit
36: Weight
41, 44, 601, 611, 612, 613: Antibacterial sheet
51: Antibacterial pad
54: Inner sheet
91, 96, 97: High-density portion
92, 95, 98: Low-density portion
100, 400, 401: Container
300, 301, 302, 303, 304: Slime removing net
500, 501, 502, 503: Adhesive plaster
614: Sheet (liquid absorbing article)
621: First principal surface
622: Second principal surface
652: Sheet (liquid impermeable sheet)

The invention claimed is:

1. A fabric comprising:
  a first yarn constructed to generate a first electric charge having a first polarity when acted upon by external energy; and
  a second yarn constructed to generate a second electric charge having a second polarity different from the first polarity when acted upon by the external energy,
  the first yarn and the second yarn arranged in at least one of a low-density portion of the fabric and/or a high-density portion of the fabric, the high-density portion having a lower porosity than the low-density portion.

2. The fabric according to claim 1, wherein the first yarn and the second yarn are each arranged both of the low-density portion and the high-density portion.

3. The fabric according to claim 2, wherein a first distance between the first yarn and the second yarn in the low-density portion is larger than a second distance between the first yarn and the second yarn in the high-density portion.

4. The fabric according to claim 3, wherein the fabric includes a first principal surface and a second principal surface opposite the first principal surface, and wherein the low-density portion is greater in thickness as measured from the first principal surface to the second principal surface than the high-density portion.

5. The fabric according to claim 2, wherein the fabric includes a first principal surface and a second principal surface opposite the first principal surface, and wherein the low-density portion is greater in thickness as measured from the first principal surface to the second principal surface than the high-density portion.

6. The fabric according to claim 1, wherein the fabric includes a first principal surface and a second principal surface opposite the first principal surface, and wherein the low-density portion is greater in thickness as measured from the first principal surface to the second principal surface than the high-density portion.

7. The fabric according to claim 1, wherein at least one of the first yarn or the second yarn comprises a core yarn and a piezoelectric film wound around the core yarn.

8. The fabric according to claim 7, wherein both the core yarn and the piezoelectric film are made from polylactic acid.

9. The fabric according to claim 7, wherein the core yarn is a conductive yarn having electrical conductivity.

10. The fabric according to claim 1, wherein both the first yarn and the second yarn each comprises a core yarn and a piezoelectric film wound around the core yarn.

11. The fabric according to claim 10, wherein both the core yarn and the piezoelectric film are made from polylactic acid.

12. The fabric according to claim 10, wherein the core yarn is a conductive yarn having electrical conductivity.

13. The fabric according to claim 1, further comprising a third yarn arranged with the first and second yarns in the fabric.

14. The fabric according to claim 13, wherein the first yarn and the second yarn are arranged as warps and the third yarn is arranged as a weft in the fabric.

15. The fabric according to claim 14, wherein the first yarn and second yarn are alternately arranged side by side in the fabric.

16. The fabric according to claim 1, wherein the first yarn and second yarn are alternately arranged side by side in the fabric.

17. The fabric according to claim 1, wherein the first yarn and second yarn are arranged together in a plating stitch in the fabric.

18. A liquid absorbing article comprising:
  the fabric according to claim 4; and
  a liquid impermeable sheet attached to one of the first principal surface or the second principal surface.

19. A liquid absorbing article comprising:
  the fabric according to claim 5; and
  a liquid impermeable sheet attached to one of the first principal surface or the second principal surface.

20. A liquid absorbing article comprising:
  the fabric according to claim 6; and
  a liquid impermeable sheet attached to one of the first principal surface or the second principal surface.

* * * * *